(12) United States Patent
Osborne et al.

(10) Patent No.: US 11,850,124 B2
(45) Date of Patent: Dec. 26, 2023

(54) DEBRIDEMENT WOUND DRESSINGS AND SYSTEMS AND METHODS USING THE SAME

(71) Applicant: KCI Licensing, Inc., San Antonio, TX (US)

(72) Inventors: Sandra N. Osborne, San Antonio, TX (US); Christopher A. Carroll, San Antonio, TX (US)

(73) Assignee: 3M Innovative Properties Company, Saint Paul, MN (US)

( * ) Notice: Subject to any disclaimer, the term of this patent is extended or adjusted under 35 U.S.C. 154(b) by 489 days.

(21) Appl. No.: 16/165,457

(22) Filed: Oct. 19, 2018

(65) Prior Publication Data

US 2019/0117465 A1    Apr. 25, 2019

Related U.S. Application Data

(60) Provisional application No. 62/576,484, filed on Oct. 24, 2017.

(51) Int. Cl.
*A61F 13/02* (2006.01)
*A61L 15/44* (2006.01)
(Continued)

(52) U.S. Cl.
CPC .. *A61F 13/00063* (2013.01); *A61F 13/00008* (2013.01); *A61F 13/00029* (2013.01);
(Continued)

(58) Field of Classification Search
CPC .......... A61F 13/00008; A61F 13/00017; A61F 13/00021; A61F 13/00029; A61F 13/00051; A61F 13/00068; A61F 2013/00327; A61F 13/0203; A61F 13/0216; A61F 15/00; A61F 2013/00927; A61F 2013/00536; A61F 2013/0028; A61F 2013/00063; A61M 27/00; A61M 1/0088; A61M 1/009; A61L 15/425; A61L 15/44; A61L 26/0066; A61L 26/008; A61L 26/0085; A61L 26/0095
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Pore definition, https://www.vocabulary.com/dictionary/pore (Year: 2022).*

(Continued)

*Primary Examiner* — Camtu T Nguyen

(57) ABSTRACT

A wound dressing that includes a contact layer having walls defining a plurality of perforations and a debriding matrix including a polymer and at least one debriding agent is provided herein. Systems, methods and kits using the wound dressing for debriding a tissue site are also provided herein.

29 Claims, 12 Drawing Sheets

(51) Int. Cl.
*A61F 13/00* (2006.01)
*A61L 15/42* (2006.01)
*A61F 17/00* (2006.01)
*A61L 26/00* (2006.01)

(52) U.S. Cl.
CPC ........ *A61F 13/00068* (2013.01); *A61F 17/00* (2013.01); *A61L 15/425* (2013.01); *A61L 15/44* (2013.01); *A61F 13/0216* (2013.01); *A61L 26/008* (2013.01); *A61L 26/0066* (2013.01); *A61L 2300/254* (2013.01)

(58) Field of Classification Search
USPC .......................................................... 602/43
See application file for complete search history.

(56) References Cited

U.S. PATENT DOCUMENTS

| | | | |
|---|---|---|---|
| 2,632,443 | A | 3/1953 | Esher |
| 2,682,873 | A | 7/1954 | Evans et al. |
| 2,910,763 | A | 11/1959 | Auterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Denbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,846,813 | A * | 7/1989 | Raley .................. A61F 13/512 604/378 |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A * | 3/1990 | Reed .................. A61L 15/58 604/389 |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Uheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A * | 12/1992 | Karami ............... A61F 13/0203 602/57 |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A * | 6/1997 | Argenta ............... A61M 1/782 602/42 |
| 5,645,081 | A | 7/1997 | Argenta et al. |
| 5,782,787 | A * | 7/1998 | Webster ................ A61F 13/023 602/56 |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,062,661 | B2 * | 11/2011 | Caldwell ................ A61F 17/00 424/448 |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 * | 9/2013 | Blott ..................... A61M 1/94 604/313 |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,227,000 | B2 * | 1/2016 | Fink ..................... A61F 13/53 |
| 9,289,542 | B2 | 3/2016 | Blott et al. |
| 10,137,037 | B2 * | 11/2018 | Tout ..................... A61M 1/915 |
| 10,406,036 | B2 * | 9/2019 | Braga ................... A61F 13/00068 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2003/0108587 | A1 * | 6/2003 | Orgill ................... A61L 15/425 424/423 |

(56) References Cited

U.S. PATENT DOCUMENTS

| | | | |
|---|---|---|---|
| 2005/0228329 A1* | 10/2005 | Boehringer | A61M 1/915 602/52 |
| 2007/0055209 A1* | 3/2007 | Patel | A61M 1/80 604/315 |
| 2007/0185463 A1* | 8/2007 | Mulligan | A61F 13/0203 424/445 |
| 2009/0069760 A1 | 3/2009 | Finklestein | |
| 2010/0030178 A1 | 2/2010 | MacMeccan et al. | |
| 2013/0045196 A1* | 2/2013 | Shi | A61L 26/0066 435/23 |
| 2014/0163491 A1 | 6/2014 | Schuessler et al. | |
| 2015/0079196 A1* | 3/2015 | Chakravarthy | A61F 13/00012 424/537 |
| 2015/0080788 A1 | 3/2015 | Blott et al. | |
| 2015/0320603 A1* | 11/2015 | Locke | A61B 17/3205 604/543 |
| 2016/0120706 A1* | 5/2016 | Collinson | A61F 13/00068 604/319 |
| 2017/0151314 A1* | 6/2017 | Salamone | A61K 38/54 |
| 2017/0231823 A1* | 8/2017 | Zawoy | A61B 17/135 604/23 |
| 2018/0310566 A1* | 11/2018 | Sawyer | A61L 17/005 |
| 2019/0328824 A1* | 10/2019 | Radisic | A61K 38/08 |
| 2020/0101208 A1* | 4/2020 | Freedman | A61M 1/85 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2311509 A1 | 4/2011 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2005/051461 A1 | 6/2005 |
| WO | 2007128985 A2 | 11/2007 |
| WO | 2008/005532 A2 | 1/2008 |
| WO | 2010038231 A1 | 4/2010 |
| WO | 2013/032745 A1 | 3/2013 |
| WO | 2015/172111 A1 | 11/2015 |
| WO | 2016/025293 A1 | 2/2016 |

OTHER PUBLICATIONS

Perforation definition, https://www.vocabulary.com/dictionary/perforation (Year: 2022).*

Globalspec_ Foams and Foam Materials Information, https://www.globalspec.com/learnmore/materials_chemicals_adhesives/composites_textiles_reinforcements/foams_foam_materials (Year: 2022).*

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al.; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

(56) References Cited

OTHER PUBLICATIONS

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion for corresponding Application No. PCT/US2018/056638, dated Jan. 29, 2019.
Chinese First Office Action Corresponding to Application No. 2018800788177, dated Jun. 20, 2021.
Japanese Notice of Rejection Corresponding to Application No. 2020-522358, dated Aug. 9, 2022.

\* cited by examiner

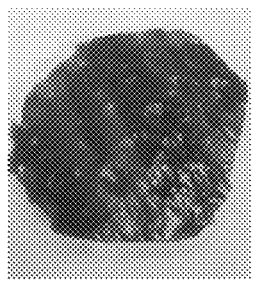 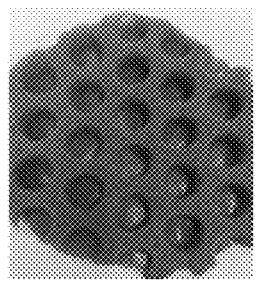 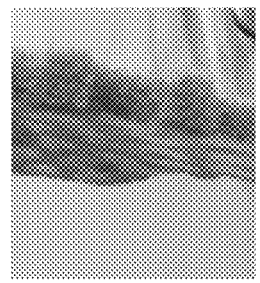 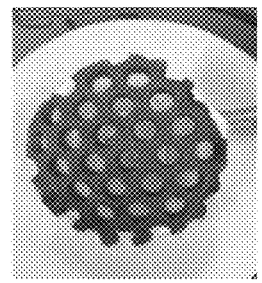
FIG. 14a   FIG. 14b   FIG. 14c   FIG. 14d
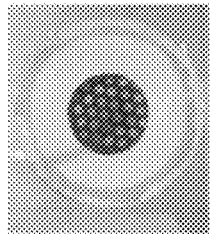 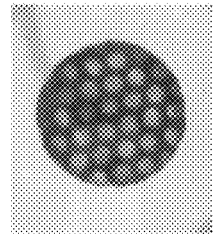 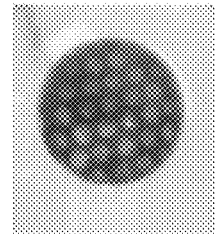 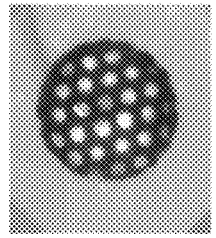
FIG. 15a   FIG. 15b   FIG. 15c   FIG. 15d
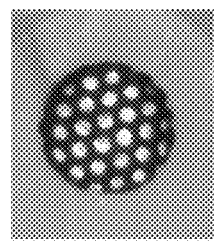 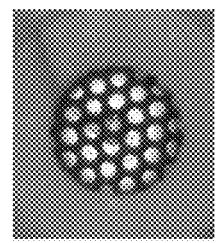
FIG. 15e   FIG. 15f

DEBRIDEMENT WOUND DRESSINGS AND SYSTEMS AND METHODS USING THE SAME

RELATED APPLICATION

This application claims the benefit, under 35 U.S.C. § 119(e), of the filing of U.S. Provisional Patent Application Ser. No. 62/576,484, entitled "DEBRIDEMENT WOUND DRESSINGS AND SYSTEMS AND METHODS USING THE SAME," filed Oct. 24, 2017, which is incorporated herein by reference for all purposes.

TECHNICAL FIELD

The invention set forth in the appended claims relates generally to tissue treatment systems and more particularly, but without limitation, to debridement wound dressings and methods and systems for debriding tissue using the debridement wound dressings.

BACKGROUND

A wide variety of materials and devices, generally characterized as "dressings," are generally known in the art for use in treating a wound or other disruption of tissue. Such wounds may be the result of trauma, surgery, or disease, and may affect skin or other tissues. In general, dressings may control bleeding, absorb wound exudate, ease pain, protect wound tissue from infection, or otherwise promote healing and protect the wound from further damage.

Debriding tissue can also be beneficial for wound healing. For example, removing necrotic tissue, biofilm, slough, eschar, and other debris from a wound can improve the efficacy and efficiency of various treatments and dressings, and reduce the risk of infection.

Additionally, clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy, debridement, and instillation therapy are known, improvements to therapy systems, components, and processes may benefit healthcare providers and patients.

BRIEF SUMMARY

Wound dressings and systems, apparatuses, and methods using such wound dressings for treating and debriding tissue in a negative-pressure therapy environment are set forth in the appended claims. Illustrative embodiments are also provided to enable a person skilled in the art to make and use the claimed subject matter.

In some embodiments, a wound dressing may be provided. The wound dressing may comprise a contact layer and a debriding matrix. The contact layer may comprise walls defining a plurality of perforations. The debriding matrix may comprise a polymer and at least one debriding agent. The debriding matrix may be operatively coupled to the contact layer.

Also, in some embodiments, a system, for example, for debriding a tissue site may be provided. The system may comprise a wound dressing as described herein and a cover adapted to form a sealed environment over the contact layer and the tissue site.

Also, in some embodiments, a method for debriding a tissue site may be provided. The method may comprise positioning the wound dressing as described herein adjacent to the tissue site. The method may also comprise positioning a cover over the contact layer and sealing the cover to tissue surrounding the tissue site to form a sealed environment enclosing the wound dressing. The method may also comprise fluidly coupling a negative-pressure source to the wound dressing and supplying negative pressure to the wound dressing to draw tissue into the perforations to form nodules.

Also, in some embodiments, a wound dressing kit may be provided. The kit may comprise a contact layer comprising walls defining a plurality of perforations and a debriding matrix comprising a polymer and at least one debriding agent. The contact layer and the debriding matrix may be separate or together.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 14a is a photograph of a first surface of Dressing 1 of Example 1.

FIG. 14b is a photograph of a second surface of Dressing 1 of Example 1.

FIG. 14c is a photograph of a side view of Dressing 1 of Example 1.

FIG. 14d is a photograph of the first surface of Dressing 1 of Example 1 after two instillation cycles and two negative pressure wound therapy (NPWT) cycles.

FIGS. 15a and 15b are photographs of the first surface of Dressing 1 of Example before the instillation and NPWT cycles.

FIG. 15c is a photograph of the first surface of Dressing 1 of Example after the first instillation cycle.

FIG. 15d is a photograph of the first surface of Dressing 1 of Example after the first NPWT cycle.

FIG. 15e is a photograph of the first surface of Dressing 1 of Example after the second instillation cycle.

FIG. 15f is a photograph of the first surface of Dressing 1 of Example after the second NPWT cycle.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

I. Therapy System

Figure 1:
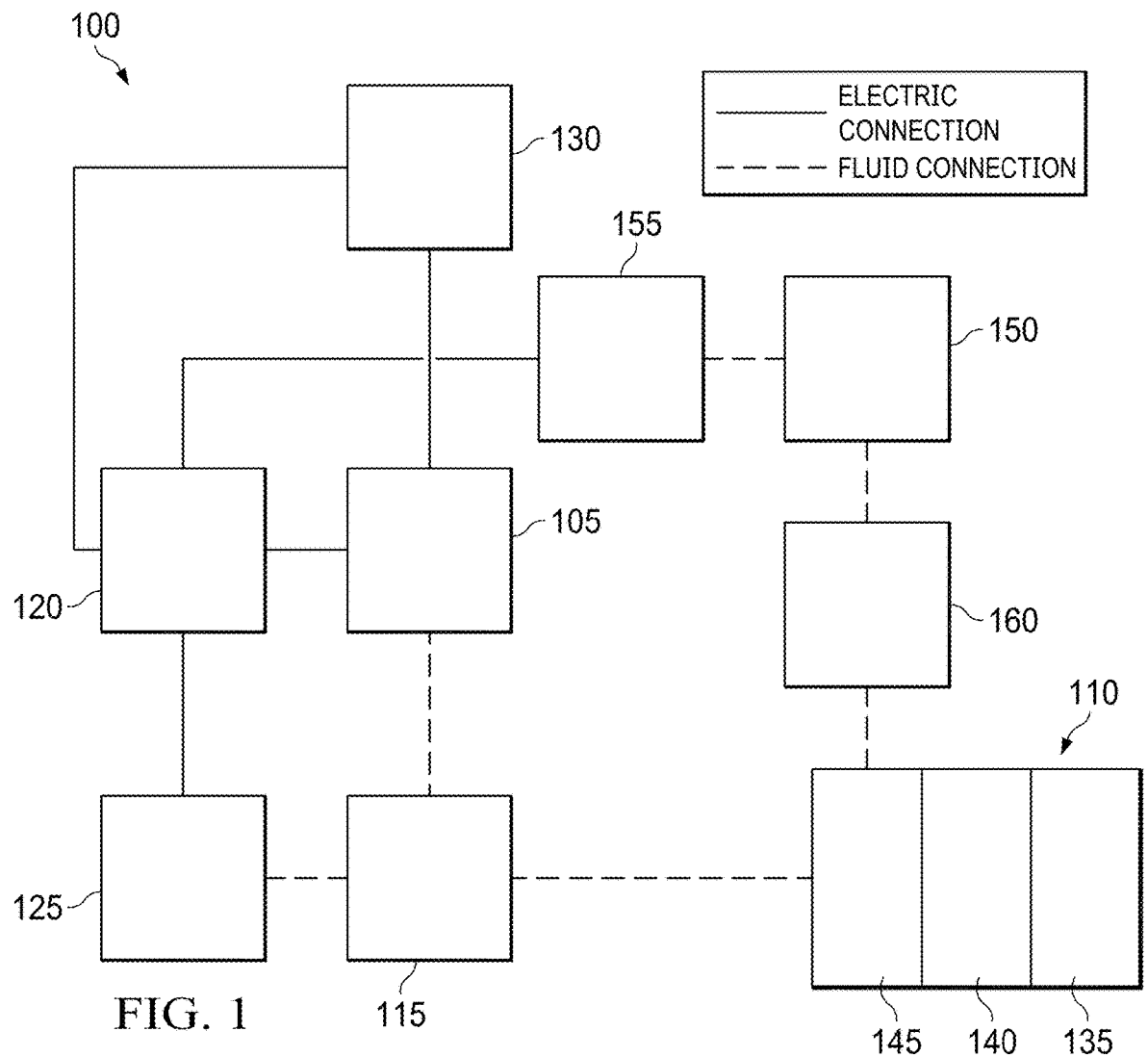
FIG. 1 is a functional block diagram of an example embodiment of a therapy system that can treat tissue in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, a wound dressing 110, a fluid container, such as a container 115, and a regulator or controller, such as a controller 120, for example. Additionally, the therapy system 100 may include sensors to measure operating parameters and provide feedback signals to the controller 120 indicative of the operating parameters. As illustrated in FIG. 1, for example, the therapy system 100 may include a pressure sensor 125, an electric sensor 130, or both, coupled to the controller 120. As illustrated in the example of FIG. 1, the wound dressing 110 may comprise or consist essentially of one or more of a debriding matrix 135, a contact layer 140 and optionally a cover 145.

The therapy system 100 may also include a source of instillation solution. For example, a solution source 150 may be fluidly coupled to the wound dressing 110, as illustrated in the example embodiment of FIG. 1. The solution source 150 may be fluidly coupled to a positive-pressure source such as the positive-pressure source 155, a negative-pressure source such as the negative-pressure source 105, or both in some embodiments. A regulator, such as an instillation regulator 160, may also be fluidly coupled to the solution source 150 and the wound dressing 110 to ensure proper dosage of instillation solution (e.g. saline) to a tissue site. For example, the instillation regulator 160 may comprise a piston that can be pneumatically actuated by the negative-pressure source 105 to draw instillation solution from the solution source during a negative-pressure interval and to instill the solution to a wound dressing during a venting interval. Additionally or alternatively, the controller 120 may be coupled to the negative-pressure source 105, the positive-pressure source 155, or both, to control dosage of instillation solution to a tissue site. In some embodiments, the instillation regulator 160 may also be fluidly coupled to the negative-pressure source 105 through the wound dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the solution source 150, the controller 120 and other components into a therapy unit.

In general, components of the therapy system 100 may be coupled directly or indirectly. For example, the negative-pressure source 105 may be directly coupled to the container 115, and may be indirectly coupled to the wound dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 120, and may be fluidly coupled to one or more distribution components to provide a fluid path to a tissue site. In some embodiments, components may also be coupled by virtue of physical proximity, being integral to a single structure, or being formed from the same piece of material.

A distribution component is preferably detachable, and may be disposable, reusable, or recyclable. The wound dressing 110 and the container 115 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a wound dressing interface may facilitate coupling a fluid conductor to the wound dressing 110. For example, such a wound dressing interface may be a SENSAT.R.A.C.™ Pad available from KCI of San Antonio, Tex.

A. Negative-Pressure Supply

A negative-pressure supply, such as the negative-pressure source 105, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

B. Container

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

C. Controller

A controller, such as the controller 120, may be a microprocessor or computer programmed to operate one or more components of the therapy system 100, such as the negative-pressure source 105. In some embodiments, for example, the controller 120 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the contact layer 140, for example. The controller 120 is also preferably configured to receive one or more input signals, such as a feedback signal, and programmed to modify one or more operating parameters based on the input signals.

D. Sensors

Sensors, such as the pressure sensor 125 or the electric sensor 130, are generally known in the art as any apparatus operable to detect or measure a physical phenomenon or property, and generally provide a signal indicative of the phenomenon or property that is detected or measured. For example, the pressure sensor 125 and the electric sensor 130 may be configured to measure one or more operating parameters of the therapy system 100. In some embodiments, the pressure sensor 125 may be a transducer configured to measure pressure in a pneumatic pathway and convert the measurement to a signal indicative of the pressure measured. In some embodiments, for example, the pressure sensor 125 may be a piezoresistive strain gauge. The electric sensor 130 may optionally measure operating parameters of the negative-pressure source 105, such as the voltage or current, in some embodiments. Preferably, the signals from the pressure sensor 125 and the electric sensor 130 are suitable as an input signal to the controller 120, but some signal conditioning may be appropriate in some embodiments. For example, the signal may need to be filtered or amplified before it can be processed by the controller 120. Typically, the signal is an electrical signal, but may be represented in other forms, such as an optical signal.

E. Wound Dressing

Wound dressings, such as wound dressing 110, may be any suitable configuration and composition. In some embodiments, the wound dressing 110 may comprise a contact layer 140 and a debriding matrix 135. In some embodiments, the debriding matrix 135 may be operatively coupled to the contact layer 140.

1. Contact Layer

The contact layer 140 can be generally adapted to partially or fully contact a tissue site. The contact layer 140 may take many forms, and may have many sizes, shapes, or thicknesses depending on a variety of factors, such as the type of treatment being implemented or the nature and size of a tissue site. For example, the size and shape of the contact layer 140 may be adapted to the contours of deep and irregular shaped tissue sites. Moreover, any or all of the surfaces of the contact layer 140 may have projections or an uneven, course, or jagged profile that can induce strains and stresses on a tissue site, which can promote granulation at the tissue site.

In some embodiments, the contact layer 140 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid such as from a source of instillation solution across a tissue site.

In some illustrative embodiments, the pathways of a manifold may be interconnected to improve distribution or collection of fluids across a tissue site. In some illustrative embodiments, a manifold may be a porous material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In other embodiments, perforated, closed-cell foam may be suitable. For example, some embodiments of the contact layer 140 may comprise or consist of closed-cell, cross-linked polyolefin foam with perforations. In some embodiments, a manifold may additionally or alternatively comprise projections that form interconnected fluid pathways. For example, a manifold may be molded to provide surface projections that define interconnected fluid pathways.

The average cell size of foam may vary according to needs of a prescribed therapy. For example, in some embodiments, the contact layer 140 may be foam having pore sizes in a range of 400-600 microns. The tensile strength of the contact layer 140 may also vary according to needs of a prescribed therapy. For example, the tensile strength of foam may be increased for instillation of topical treatment solutions. In some examples, the contact layer 140 may be reticulated polyurethane foam such as found in GRANUFOAM™ dressing or V.A.C. VERAFLO™ dressing, both available from KCI of San Antonio, Tex.

In some embodiments, the contact layer 140 may be formed from material that is mechanically or chemically compressed to increase density at ambient pressure. For example, the contact layer 140 may comprise or consist of a compressible material, such as a foam that has been compressed. Compressed foam may be characterized by a firmness factor that is defined as a ratio of the density of foam in a compressed state to the density of the same foam in an uncompressed state. In some embodiments, the contact layer 140 may have a firmness factor of about 1 to about 10. For example, compressed foam having a density that is five times greater than a density of the same foam in an uncompressed state may be characterized as having a firmness factor of 5. Increasing the firmness factor of foam may increase a stiffness of the foam in a direction that is parallel to a thickness of the foam. For example, increasing the firmness factor of the contact layer 140 may increase a stiffness of the contact layer 140 in a direction that is parallel to the thickness of the contact layer 140. In some embodiments, the contact layer 140 may comprise or consist of compressed reticulated polyurethane foam, and may have a density of about 0.03 grams per centimeter3 (g/cm3) in its uncompressed state. If the foam is compressed to have a firmness factor of 5, the foam may be compressed until the density of the foam is about 0.15 g/cm3. In some embodiments, the contact layer 140 may comprise or consist of a compressed foam have a thickness between about 4 millimeters to about 15 millimeters, and more specifically, about 8 millimeters at ambient pressure.

Generally, compressed foam exhibits less deformation under negative pressure than a similar uncompressed foam. The decrease in deformation may be caused by the increased stiffness as reflected by the firmness factor. If subjected to the stress of negative pressure, compressed foam may flatten less than uncompressed foam of similar material. In some examples, if the thickness of the contact layer 140 is about 8 millimeters at ambient pressure, the contact layer 140 may have a thickness between about 1 millimeter and about 5 millimeters under therapeutic levels of negative pressure, and, generally, greater than about 3 millimeters. The stiffness of compressed foam in the direction parallel to the thickness of the foam may allow the foam to be more compliant or compressible in other directions, such as directions perpendicular to the thickness.

The contact layer 140 may be either hydrophobic or hydrophilic. In an example in which the contact layer 140 may be hydrophilic, the contact layer 140 may also wick fluid away from a tissue site, while continuing to distribute negative pressure to the tissue site. The wicking properties of the contact layer 140 may draw fluid away from a tissue site by capillary flow or other wicking mechanisms. An example of a hydrophilic foam is a polyvinyl alcohol, open-cell foam such as V.A.C. WHITEFOAM™ dressing available from KCI of San Antonio, Texas. Other hydrophilic foams may include those made from polyether. Other foams that may exhibit hydrophilic characteristics include hydrophobic foams that have been treated or coated to provide hydrophilicity.

The contact layer 140 may further promote granulation at a tissue site when pressure within the sealed therapeutic environment is reduced. For example, any or all of the surfaces of the contact layer 140 may have an uneven, coarse, or jagged profile that can induce microstrains and stresses at a tissue site if negative pressure is applied through the contact layer 140.

In some embodiments, the contact layer 140 may be constructed from resorbable or bioresorbable materials. As used herein, the terms "resorbable" or "bioresorbable" are synonymous and refer to the ability of at least a portion of a material to disintegrate, degrade, or dissolve upon exposure to physiological fluids or processes such that at least a portion of the material may be absorbed or assimilated, for example, at a tissue site or in vivo in a mammalian body. Resorbability or bioresorbability may be exhibited as a result of a chemical process or condition, a physical process or condition, or combinations thereof. Suitable bioresorbable materials may include, without limitation, a polymeric blend of polylactic acid (PLA) and polyglycolic acid (PGA). The polymeric blend may also include without limitation polycarbonates, polyfumarates, and capralactones. The contact layer 140 may further serve as a scaffold for new cell-growth, or a scaffold material may be used in conjunction with the contact layer 140 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the contact layer 140 may be formed from thermoplastic elastomers (TPE), such as styrene ethylene butylene styrene (SEBS) copolymers, or thermoplastic polyurethane (TPU). The contact layer 140 may be formed by combining sheets of TPE or TPU. In some embodiments, the sheets of TPE or TPU may be bonded, welded, adhered, or otherwise coupled to one another. For example, in some embodiments, the sheets of TPE or TPU may be welded using radiant heat, radio-frequency welding, or laser welding. Supracor, Inc., Hexacor, Ltd., Hexcel Corp., and Econocorp, Inc. may produce suitable TPE or TPU sheets for the formation of the contact layer 140. In some embodiments, sheets of TPE or TPU having a thickness between about 0.2 mm and about 2.0 mm may be used to form a structure suitable for the contact layer 140. In some embodiments, the contact layer 140 may be formed from a 3D textile, also referred to as a spacer fabric. Suitable 3D textiles may be produced by Heathcoat Fabrics, Ltd., Baltex, and Mueller Textil Group. The contact layer 140 can also be formed from felted foam, polyurethane, silicone, polyvinyl alcohol, and metals, such as copper, tin, silver or other beneficial metals.

Figure 2:
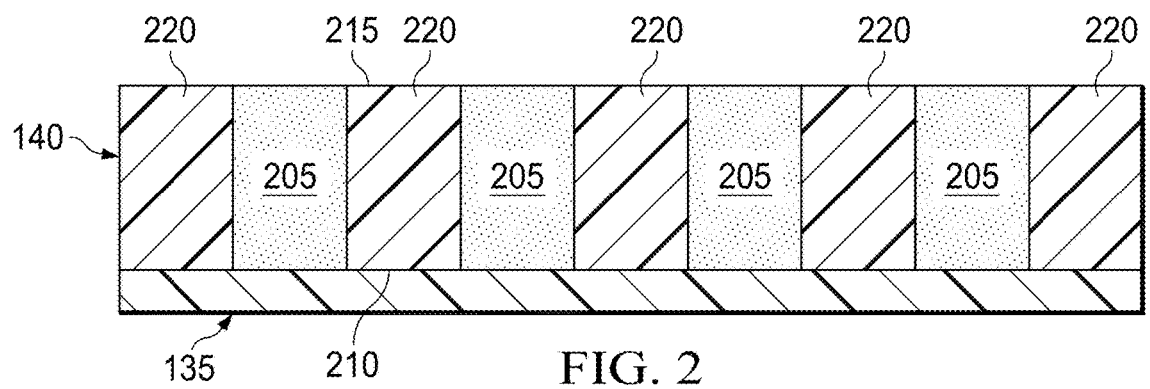
FIG. 2 is a schematic section view of an example of a dressing that may be associated with an example embodiment of therapy system of FIG. 1.

FIG. 2 is a schematic section view of an example of the wound dressing 110, including an example of the debriding matrix 135 and an example of the contact layer 140, illustrating additional details that may be associated with some embodiments.

In some embodiments, the contact layer 140 may have a substantially uniform thickness. A thickness between about 5.0 mm to about 20 mm or about 5.0 mm to about 20 mm may be suitable for some configurations. For example, some embodiments of the contact layer 140 may have a thickness of about 8 millimeters. In some embodiments, the thickness may not be strictly uniform. For example, a tolerance of about 2 millimeters may be suitable for some embodiments.

In some embodiments, the contact layer 140 may have one or more perforations 205. In general, the perforations 205 may extend through the contact layer 140. As illustrated in FIG. 2, for example, one or more of the perforations 205 may be a through-hole that extends through the contact layer 140 from a first surface 210 to a second surface 215.

In other embodiments, one or more of the perforations 205 may be a blind hole, which does not pass completely through the contact layer 140. For example, one or more of the perforations may extend into the contact layer 140 from the first surface 210 and have a depth that is less than the thickness of the contact layer 140.

The perforations 205 may form walls 220 in the contact layer 140. In some embodiments, an interior surface of the walls 220 may be generally perpendicular to the first surface 210 and the second surface 215 of the contact layer 140. In still other embodiments, the walls 220 may have a substantially smooth surface between the first surface 210 and the second surface 215 of the contact layer 140. In still other embodiments, the perforations 205 may be tapered, and may have conical, pyramidal, or other irregular geometries. In some embodiments, the perforations 205 may be formed so that a central axis of each of the perforations 205 is orthogonal to the first surface 210, the second surface 215, or both. In other embodiments, one or more of the perforations 205 may be formed so that the central axis is oblique to the first surface 210, the second surface 215, or both.

Figure 3:
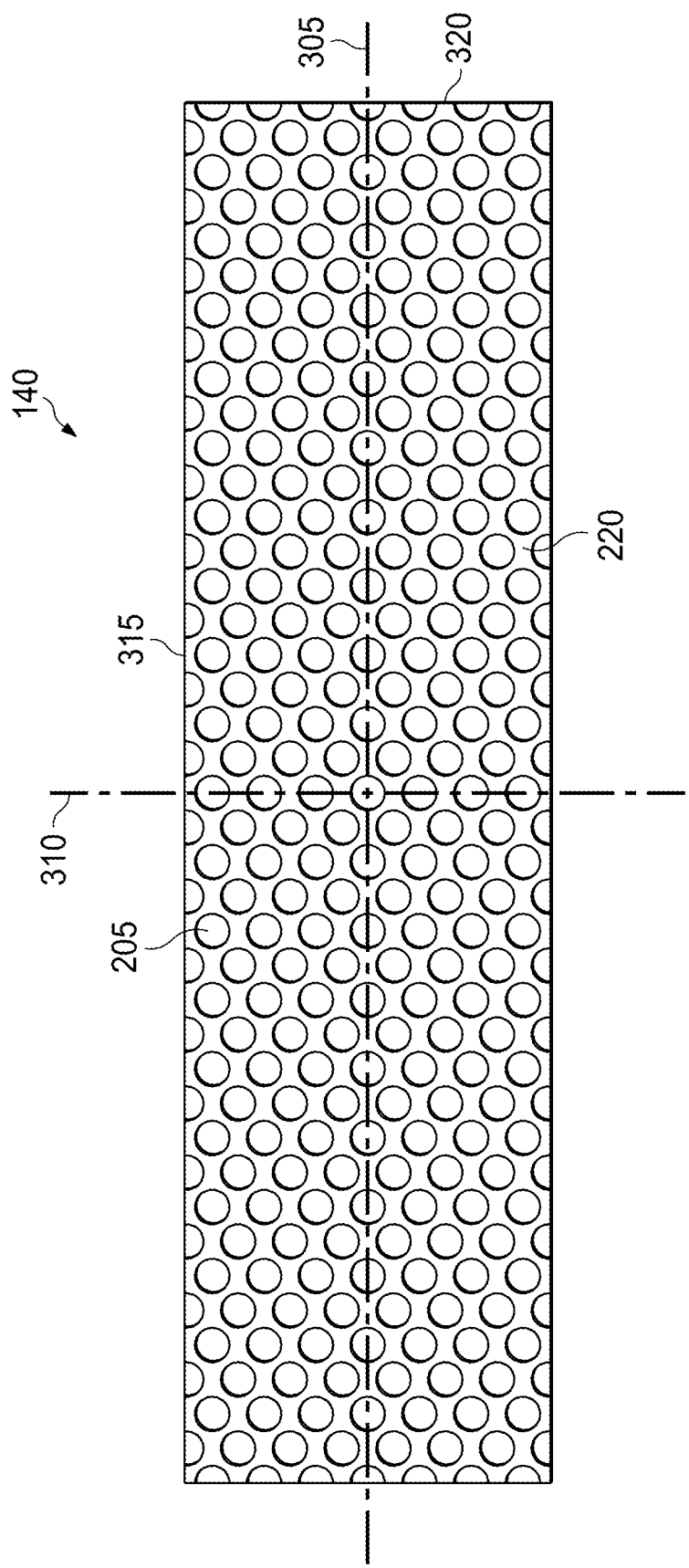
FIG. 3 is a plan view of an example of a contact layer that may be associated with some embodiments of a dressing.

FIG. 3 is a plan view of an example of the contact layer 140, illustrating additional details that may be associated with some embodiments. For example, some embodiments of the perforations 205 may have a circular cross-section as illustrated in FIG. 3. In some embodiments, the perforations 205 may have an average diameter of greater than about 2.0 mm, greater than about 4.0 mm, greater than about 6.0 mm, greater than about 10 mm or an average diameter between about 5 mm and about 20 mm, and in some embodiments, the average diameter of the perforations 205 may be about 10 mm.

In some embodiments, the contact layer 140 may have a first orientation line 305 and a second orientation line 310 that is perpendicular to the first orientation line 305. The first orientation line 305 and the second orientation line 310 may be lines of symmetry through the contact layer 140. In the example of FIG. 3, the contact layer 140 has a generally rectangular shape with longitudinal edges 315 and latitudinal edges 320. In some embodiments, the first orientation line 305 may be parallel to the longitudinal edges 315.

In some embodiments, the longitudinal edges 315 and the latitudinal edges 320 of the contact layer 140 may not be straight edges. For example, one or more of the perforations 205 may overlap the longitudinal edges 315 or the latitudinal edges 320, causing the edge to have a non-linear profile, which may reduce the disruption of keratinocyte migration and enhance re-epithelialization while negative pressure is applied to the wound dressing 110.

The contact layer 140 may also have a variety of other suitable shapes. For example, the contact layer 140 may have a diamond, square, or circular shape. In some embodiments, the shape of the contact layer 140 may be selected to accommodate the shape or type of a tissue site. For example, the contact layer 140 may have an oval or circular shape to accommodate an oval or circular tissue site.

Figure 4:
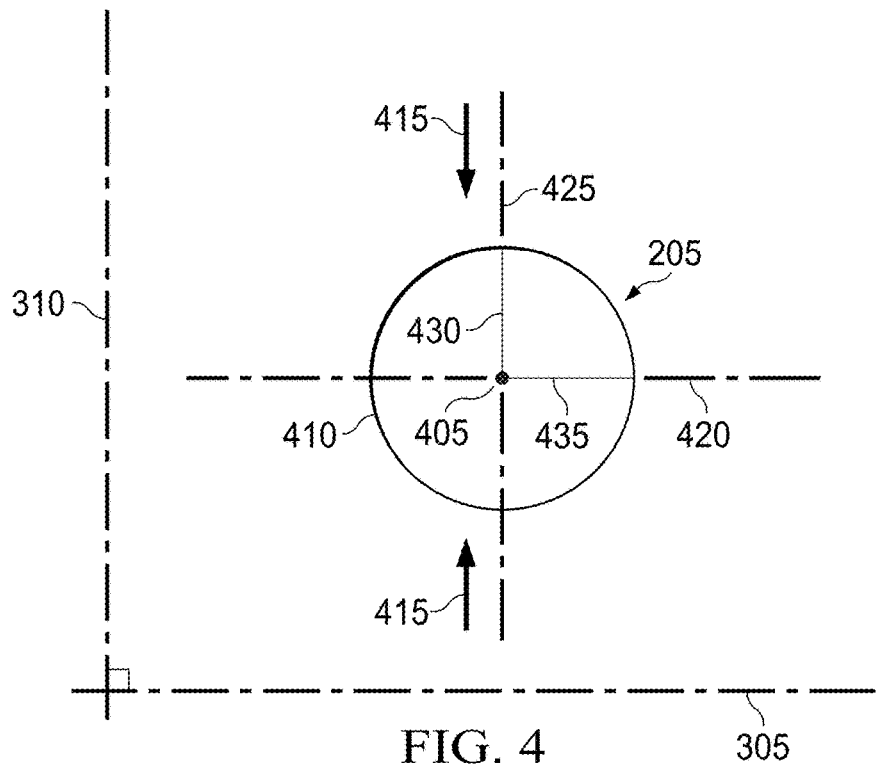
FIG. 4 is a detail view of the contact layer of FIG. 3, illustrating additional details that may be associated with some embodiments.

FIG. 4 is a detail view of one of the perforations 205 of FIG. 3, illustrating additional details that may be associated with some embodiments. As illustrated in the example of FIG. 4, one or more of the perforations 205 may include a center 405 and a perimeter 410. Each of the perforations 205 may also be characterized by a shape factor. The shape factor may represent an orientation of each of the perforations 205 relative to the first orientation line 305 and the second orientation line 310. Generally, the shape factor is a ratio of ½ a maximum dimension that is parallel to the desired direction of contraction to ½ a maximum dimension that is perpendicular to the desired direction of contraction. For example, the desired direction of contraction in FIG. 4 may be parallel to the second orientation line 310, as indicated by vector 415. A first axis 420 may pass through the center 405 parallel to the first orientation line 305, and a second axis 425 may extend through the center 405 parallel to the second orientation line 310. The shape factor of each of the perforations 205 may be defined as a ratio of a first line segment 430 on the second axis 425 extending from the center 405 to the perimeter 410, to a second line segment 435 on the first axis 420 extending from the center 405 to the perimeter 410. For example, if a length of the first line segment 430 is 2.5 mm and the length of the second line segment 435 is 2.5 mm, the shape factor would be 1. In other embodiments, the perforations 205 may have other shapes and orientations, for example, oval, hexagonal, elliptical, circular, square, triangular, conical, or amorphous or irregular or a combination thereof and be oriented relative to the first orientation line 305 and the second orientation line 310 so that the shape factor may range from about 0.5 to about 1.10.

Figure 5:
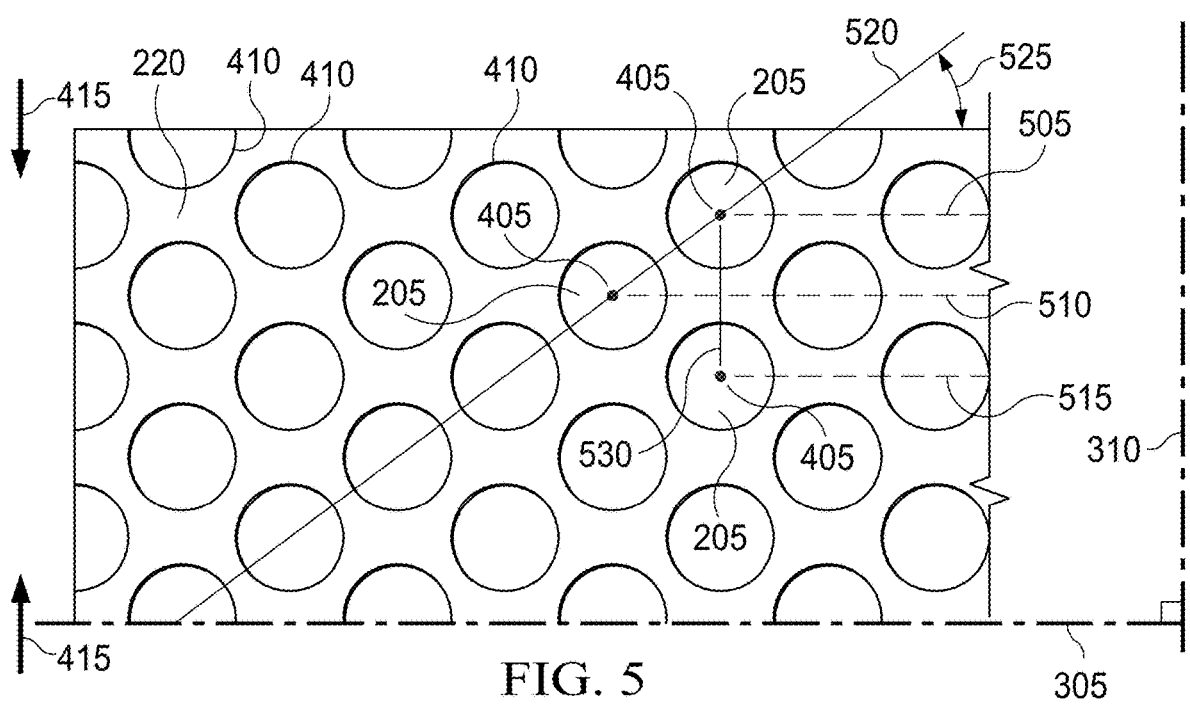
FIG. 5 is another detail view of a portion of the contact layer of FIG. 3, illustrating additional details that may be associated with some embodiments.

FIG. 5 is a detail view of a portion of the perforations 205 of FIG. 3, illustrating additional details that may be associated with some embodiments. In some embodiments, the perforations 205 may be aligned in parallel rows, for example two or more parallel rows, to form an array, as illustrated in the example of FIG. 5. For example, an array of the perforations 205 may include a first row 505, a second row 510, and a third row 515. In some embodiments, a width of the walls 220 between the perimeter 410 of two or more of the perforations 205 in a row, such as the first row 505, may be about 5 millimeters. The center 405 of each of the perforations 205 in adjacent rows, for example, the first row 505 and the second row 510, may be characterized as being offset along the first orientation line 305. In some embodiments, a strut line 520 passing through the center 405 of each of the perforations 205 in adjacent rows may define a strut angle 525 with the first orientation line 305. In some embodiments, the strut angle 525 may be less than about 90°. In other embodiments, the strut angle 525 may be between about 30° and about 70°. In other embodiments, the strut angle 525 may be about 66°. Generally, as the strut angle 525 decreases, a stiffness of the contact layer 140 in a direction parallel to the first orientation line 305 may increase. Increasing the stiffness of the contact layer 140 parallel to the first orientation line 305 may increase the compressibility of the contact layer 140 perpendicular to the first orientation line 305.

In some embodiments, the center 405 of each of the perforations 205 in alternating rows may be spaced apart parallel to the second orientation line 310 by a length 530. In some embodiments, the length 530 may be greater than an effective diameter of the perforations 205. In some embodiments, the length 530 may be between about 7 mm and about 25 mm.

The contact layer 140 may additionally or alternatively be characterized by a void-space percentage, which reflects a ratio of the void space in the first surface 210 created by the perforations 205 to the area defined by the perimeter of the contact layer 140. In general, the void-space percentage can be designed to achieve a desirable balance between handling characteristics and flexibility. For example, increasing the void-space percentage may increase the contraction characteristics of the perforations 205, and may also decrease the handling characteristics of the contact layer 140. A void-space percentage between about 40% and about 75% may be suitable for some embodiments. For example, some embodiments may have a void-space percentage of about 55%.

In some embodiments, the perforations 205 may have an effective diameter between about 3 millimeters and about 20 millimeters. An effective diameter of a non-circular area is a diameter of a circular area having the same surface area as the non-circular area. In some embodiments, one or more of the perforations 205 have a non-circular cross-section with an effective diameter of about 3.5 mm. In other embodiments, the perforations 205 may have an effective diameter between about 5 mm and about 20 mm.

Generally, the perforations 205 are not formed by a foaming process, and can be distinguished from pores or cells of material forming the contact layer 140. For example, a single pore or cell of the material is generally not large enough to extend completely through the contact layer 140. An effective diameter of the perforations 205 may be an order of magnitude larger than the effective diameter of the pores or cells of a material forming the contact layer 140. In some embodiments, the effective diameter of the perforations may be larger than about 1 mm, while the material of the contact layer 140 may be foam having a pore size less than about 600 microns.

In some embodiments, the perforations 205 may be formed during molding of the contact layer 140. In other embodiments, the perforations 205 may be formed by cutting, melting, drilling, or vaporizing the contact layer 140 after the contact layer 140 is formed. For example, a through-hole may be formed by reaming, drilling, or milling a hole completely through the contact layer 140. Additionally or alternatively, the perforations 205 may be laser-cut into the contact layer 140.

In some embodiments, formation of the perforations 205 may thermoform the material of the contact layer 140, causing the interior surface of the perforations 205 to be non-porous. For example, laser-cutting the perforations 205 into the contact layer 140 may plastically deform the material of the contact layer 140, closing any pores on the interior surfaces of the perforations 205. Alternatively or additionally, a smooth interior surface of the perforations 205 may be formed by a applying or coating a smooth material to the perforations 205. In some embodiments, a smooth interior surface may limit or otherwise inhibit ingrowth of tissue into the contact layer 140 through the perforations 205.

2. Debriding Matrix

As illustrated in the example of FIG. 2, the debriding matrix 135 can be disposed adjacent to or adhered to a surface of the contact layer 140 in some embodiments. For example, the debriding matrix 135 may be in the form of a continuous or non-continuous coating, film, gel, layer and/or sheeting, which may be adhered, fixed, fastened, or joined on the contact layer 140. In some embodiments, the debriding matrix 135 may be a coating on at least a portion of a surface of the contact layer 140, for example, the debriding matrix 135 may be coated on at least about 10%, at least about 25%, at least about 50%, at least about 75% or at least about 95% of a surface of the contact layer 140. In some embodiments, the debriding matrix 135 may be a coating on substantially an entire surface of the contact layer 140, for example, the debriding matrix 135 may be coated on at least about 99%, 99.9% or about 100% of a surface of the contact layer 140.

In some embodiments, the debriding matrix 135 may only cover a portion of the perforations 205, thus at least a portion of the perforations 205 may not be covered by the debriding matrix 135. In other embodiments, the debriding matrix 135 may be a solid sheet, covering the perforations 205 as illustrated in the example of FIG. 2. In other embodiments, the debriding matrix 135 may at least partially fill at least a portion of the perforations 205 or at least partially fill substantially all of the perforations 205. Alternatively, the debriding matrix 135 may substantially fill at least a portion of the perforations 205 or substantially fill substantially all of the perforations 205. In some embodiments, the debriding matrix 135 may be at least partially removable or separable from the contact layer 140. For example, the debriding matrix 135 can be removed from the contact layer 140 and applied directly to a tissue site.

The thickness of the debriding matrix 135 may vary. A thickness in a range of about 1.0 mm to about 10 mm, about 1.0 mm to about 5.0 mm, or about 1.0 mm to about 3.0 mm may be suitable for some embodiments. In some embodiments, the debriding matrix 135 may be porous, or may have perforations, slits, fenestrations, fluid pathways or other means for fluid flow through the debriding matrix 135.

In various embodiments, the debriding matrix 135 may comprise at least one debriding agent and a polymer. In some embodiments, the debriding matrix 135 may have a pH of about 2 to about 10 or a lower pH, for example, a pH of about 1.0 to about 6.0 a pH of about 2.0 to about 5.0, or a pH of about 2.5 to about 4.0, wherein a lower pH may further aid in wound healing. The debriding agent may be any enzyme capable of debriding a tissue site or wound. As used herein, the term "debriding" or "debridement" refers to the softening, weakening, removal, detachment and/or disruption of tissue and/or cells, such as necrotic tissue, biofilm, slough, eschar, and other debris from a tissue site, for example a wound, which can promote healing and/or reduce risk of infection. In some embodiments, the debriding agent advantageously may be active (i.e., causing debridement or disruption of tissue) across a broad pH range, for example, a pH of about 2 to about 12, or about 2 to about 10, for example, within a tissue site or wound. The debriding agent may be present in varying concentrations and/or United States Pharmacopeia units (USP units) of activity, for example, about 0.25 USP units to about 1,000 USP units, about 0.25 USP units to about 500 USP units, about 0.25 USP units to about 300 USP units or about 30 USP units to about 300 USP units. In some embodiments, the debriding agent may present in advantageously higher concentrations and/or USP units of activity for enhanced debridement. In some embodiments, the debriding agent may be selected from the group consisting of papain, urea, streptokinase, streptodornase, trypsin, collagenase, fibrinolysin, deoxyribonuclease (DNase), fibrinolysin with DNase (fibrinolysin/DNase), bromelain, and a combination thereof.

The polymer may be any suitable organic polymer for immobilizing the debriding agent therein. Additionally, the polymer may be biodegradable. As used herein, the term "biodegradable" refers to a material that is capable of chemically and/or physically deteriorating or breaking down, for example, upon exposure to a tissue site and/or physiological fluids or processes. "Biodegrading" includes tearing, breaking, severing, fracturing, dissolving, dissociating, and the like. Terms such as "soluble," "dissolvable," "dissociable," "tearable," "breakable," "severable," "fracturable," "disruptable" and the like, may be used and refer to materials that are capable of biodegrading. Biodegrading may be exhibited as a result of a chemical process or condition, a physical process or condition, or combinations thereof. Examples of suitable polymers include, but are not limited to polysaccharides (e.g., citrus fruit pectin, starches, fecula, agar), proteins (e.g., collagen, gelatin, albumin), vegetable gums (e.g., xantham gum, locust bean, guar), and combinations thereof Additionally or alternatively, the polymer may be bioresorbable.

Depending on desired solubility during use, for example, during instillation cycles, the polymer may have a soluble solid composition of at least about 10%, for example, from about 10% to about 90% or 10% to about 70%. For example, at least about 10% of the polymer may be soluble in an aqueous solution, for example, having a pH of about 2 to about 10. The polymer and/or the debriding matrix 135 may be capable of biodegrading or dissolving during use, for example, when contacted with a tissue site to release the debriding agent, which may debride the tissue site. Complete biodegrading or dissolving of the polymer is not necessary for debriding of the tissue site to occur. Rather, debriding of the tissue site may occur during one of more of the following: when the debriding matrix 135 initially contacts a tissue site; while the polymer biodegrades or dissolves; once the polymer ceases biodegrading or dissolving; and after the polymer has substantially biodegraded or dissolved. Following biodegrading or dissolving of the polymer, release of the debriding agent and/or debriding of the tissue site, the debriding agent and any remaining polymer can be advantageously washed away, for example during instillation therapy at desired time intervals, along with any wound debris. In some embodiments, the polymer and/or the debriding matrix 135 may dissolve at varying rates, for example, as quickly or as slowly as desired. For example, the polymer and/or the debriding matrix 135 may dissolve in a matter of minutes (e.g., 1, 2, 3, 4, 5 minutes, etc.), for example during one therapy cycle, or the polymer and/or the debriding matrix 135 may dissolve over the course of one or more days, for example until an endpoint in therapy.

In some embodiments, the debriding matrix 135 may further comprise one or more of a drying agent, a thickening agent, and slow release agent in varying amounts. Examples of suitable drying agents include, but are not limited to silica gel (e.g., silica xerogel, silica gel fibers), magnesium aluminum silicate, calcium oxide, calcium sulfate, a sulfonate, and combinations thereof. Examples of suitable thickening agents include, but are not limited to glycerol, glycerin, a carbomer, polyethylene glycol and combinations thereof. Without being bound by theory, it is believed that drying and/or thickening agents can aid in disrupting, removing or detaching wound debris by exerting a superficial desiccating and/or denaturing action. Such dessicating and/or denaturing activity along with mechanical action of the wound dressing can exhibit co-action or synergy in disrupting, removing or detaching wound debris.

In other embodiments, the debriding matrix 135 may further comprise oxidized cellulose. The term "oxidized cellulose" refers to any material produced by the oxidation of cellulose, for example with dinitrogen tetroxide. Such oxidation converts primary alcohol groups on the saccharide residues to carboxylic acid groups, forming uronic acid residues within the cellulose chain. The oxidation generally does not proceed with complete selectivity, and as a result hydroxyl groups on carbons 2 and 3 are occasionally converted to the keto form. These keto units introduce an alkali-labile link, which at pH 7 or higher initiates the decomposition of the polymer via formation of a lactone and sugar ring cleavage. As a result, oxidized cellulose is biodegradable and resorbable or bioresorbable under physiological conditions. In some embodiments, oxidized cellulose present in the debriding matrix 135 may be oxidized regenerated cellulose (ORC), which may be prepared by oxidation of a regenerated cellulose, such as rayon. It has been known that ORC has haemostatic properties. ORC has been available as a haemostatic fabric called SURGICEL® (Johnson & Johnson Medical, Inc.) since 1950. This product may be produced by the oxidation of a knitted rayon material.

In some embodiments, additional layers or components may be present in the wound dressing. For example, at least one further layer or component may be present between the contact layer 140 and the debriding matrix 135, at least one further layer or component may be present adjacent to a surface of the debriding matrix 135 opposed to a surface of the debriding matrix 135 adjacent to the contact layer 140, and/or at least one further layer or component may be present adjacent to a surface of the contact layer 140 opposed to a surface of contact layer 140 adjacent to the debriding matrix 135.

F. Cover

Referring back to FIG. 1, in some embodiments, a cover 145 may be provided in the wound dressing 110. A cover may provide a bacterial barrier and protection from physical trauma. In some embodiments, the cover 145 may also be constructed from a material that can reduce evaporative losses and provide a fluid seal between two components or two environments, such as between a therapeutic environment and a local external environment. The cover 145 may be, for example, an elastomeric film or membrane that can provide a seal adequate to maintain a negative pressure at a tissue site for a given negative-pressure source. The cover 145 may have a high moisture-vapor transmission rate (MVTR) in some applications. For example, the MVTR may be at least 300 g/m² per twenty-four hours in some embodiments. In some example embodiments, the cover 145 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

G. Attachment Device

An attachment device may be used to attach the cover 145 to an attachment surface, such as undamaged epidermis, a gasket, or another cover. The attachment device may take many forms. For example, an attachment device may be a medically-acceptable, pressure-sensitive adhesive configured to bond the cover 145 to epidermis around a tissue site. In some embodiments, for example, some or all of the cover 145 may be coated with an adhesive, such as an acrylic adhesive, which may have a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

H. Solution Source

The solution source 150 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

II. Methods of Use

Methods of using the wound dressings and systems as described herein are provided for debriding tissue to aid in wound healing.

In some embodiments, a method for debriding a tissue site is provided. The method may comprise positioning a wound dressing as described herein adjacent to a tissue site. The debriding matrix and the contact layer may be positioned separately or together, such that the debriding matrix may be adjacent to the tissue site and the contact layer may be adjacent to the debriding matrix. For example, a separate debriding matrix or a debriding matrix which has been separated, for example, peeled away, from a contact layer may be positioned adjacent to the tissue site followed by positioning of the contact layer adjacent to the debriding matrix. Alternatively, the wound dressing with the debriding matrix operatively coupled to the contact layer may be positioned adjacent to the site. In other embodiments, the wound dressing, for example, the contact layer and/or the debriding matrix, optionally may be customized prior to positioning adjacent to the tissue site. Customizing may include cutting and/or sizing the wound dressing as needed for use with the tissue site. For example, the contact layer and the debriding matrix may be customized either separately or together as needed and then positioned on the tissue site. Once positioned adjacent to the tissue site, at least a portion of debriding matrix may biodegrade or dissolve and continue to biodegrade or dissolve throughout the method. In some embodiments, substantially all of the debriding matrix may biodegrade or dissolve during the method.

In some embodiments, the method may further comprise positioning a sealing member, for example, a cover, over the wound dressing. In some embodiments, a filler optionally may be positioned over or adjacent to the contact layer such that the filler may be disposed between the cover and the contact layer. Additionally, the method may further comprise sealing the cover to the tissue site, for example, to tissue surrounding the tissue site, to form a sealed environment enclosing the wound dressing. Negative pressure may be supplied to the wound dressing during the method, for example, to draw tissue into perforations present in the contact layer to form nodules. In some embodiments, instillation therapy may be combined with negative-pressure therapy. In some embodiments, the method may further comprise fluidly coupling a solution source to the sealed environment and providing fluid to the sealed environment. For example, following a period of supplying negative-pressure, fluid may be supplied from the solution source to the sealed environment. In some embodiments, the method may further comprise removing the fluid from the sealed environment. The fluid removed may comprise one or more of at least a portion of one or more debriding agents, at least a portion of the polymer and at least a portion of any further components, such as thickening agents and/or drying agents, of the debriding matrix.

Figure 6:
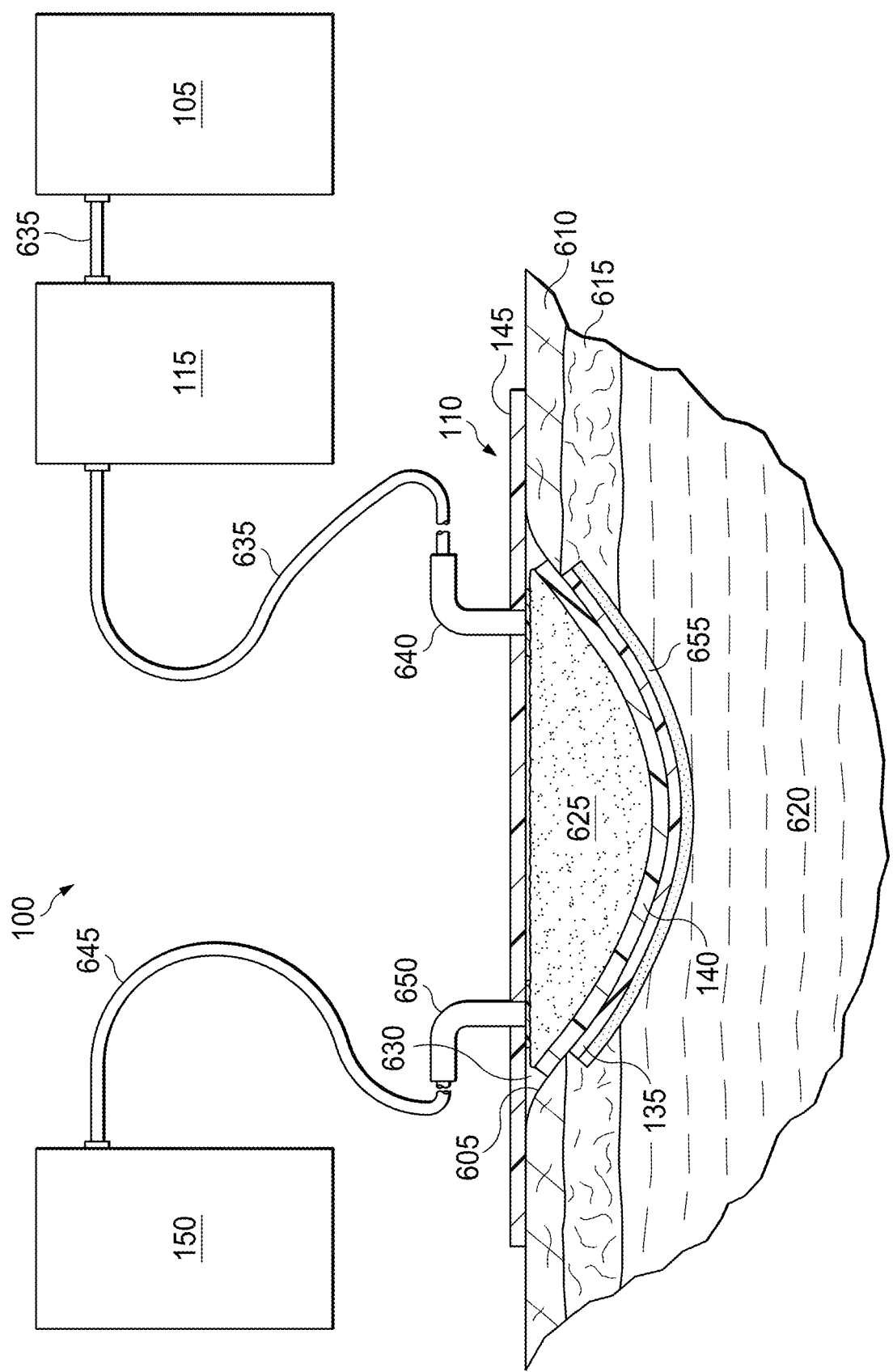
FIG. 6 is a schematic diagram of an example of the therapy system 100, illustrating additional details that may be associated with some embodiments.
Figure 7:
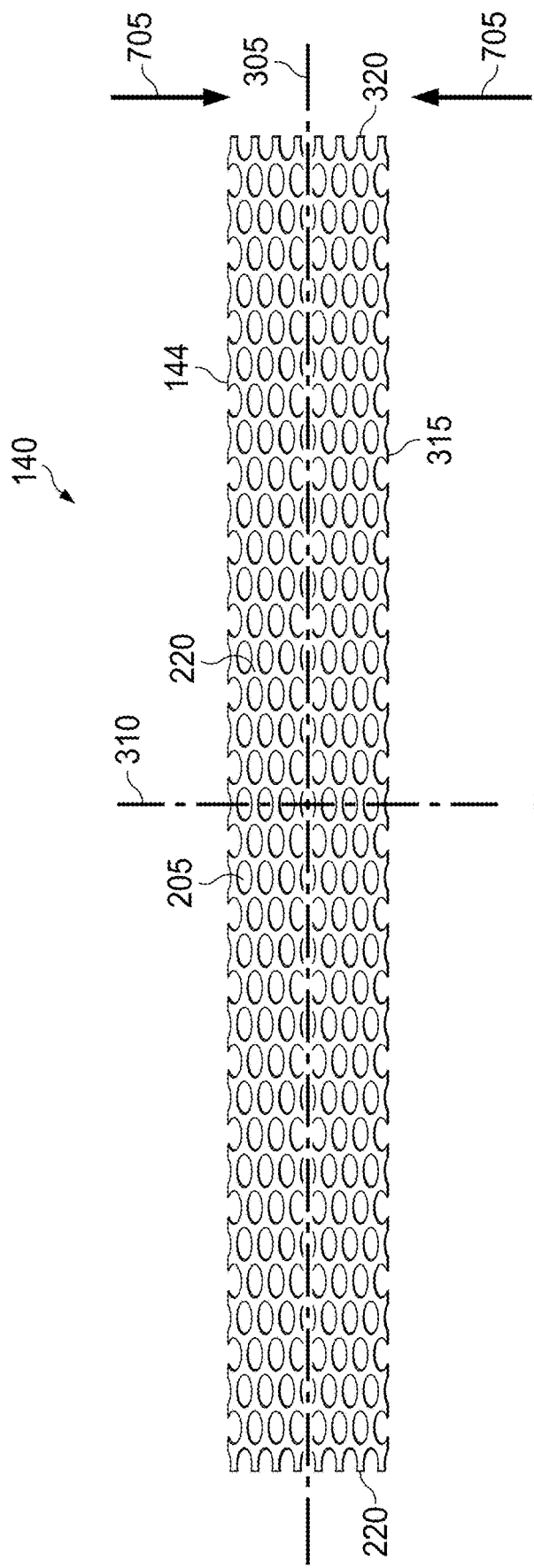
FIG. 7 is a plan view of the contact layer of FIG. 3 contracting under negative pressure.

FIG. 6 is a schematic diagram of an example of the therapy system 100, illustrating additional details that may be associated with some methods of using the therapy system 100. In operation, the debriding matrix 135, the contact layer 140, or both may be placed within, over, on, or otherwise proximate to a tissue site 605. The tissue site 605 may, for example, extend through portions of an epidermis 610, a dermis 615, and into subcutaneous tissue 620. In the example of FIG. 6, the debriding matrix 135 is positioned adjacent to the tissue site 605, and the contact layer 140 is disposed adjacent to the debriding matrix 135. As shown in FIG. 7, the first orientation line 305 and the second orientation line 310 may be used to orient the desired directions of contraction of the contact layer 140. For example, the desired direction of contraction may be parallel to the second orientation line 310 and perpendicular to the first orientation line 305. In other embodiments, the desired direction of contraction may be parallel to the first orientation line 305 and perpendicular to the second orientation line 310. In still other embodiments, the desired direction of contraction may be at an oblique angle to both the first orientation line 305 and the second orientation line 310. In other embodiments, the contact layer 140 may not have a desired direction of contraction. Optionally, a filler 625 may also be disposed adjacent to the contact layer 140, which may be useful for deep wounds. The filler 625 may be a manifold, such as a reticulated foam. The cover 145 may be placed over the debriding matrix 135 and the contact layer 140, and can be sealed to an attachment surface near the tissue site 605. For example, the cover 145 may be sealed to as tissue surrounding the tissue site 605, such as undamaged epidermis peripheral to the tissue site 605. Thus, the wound dressing 110 can provide a sealed environment 630 proximate to the tissue site 605, substantially isolated from the external environment.

The negative-pressure source 105 can be fluidly coupled to the sealed environment 630 between the cover 145 and the tissue site 605. As illustrated in the example of FIG. 6, the negative-pressure source 105 can be fluidly coupled to the contact layer 140 through first fluid conductors 635 and a first dressing interface 640 in some embodiments. The negative-pressure source 105 can reduce the pressure in the sealed therapeutic environment. Negative pressure applied across the tissue site 605 through the contact layer 140 in the sealed therapeutic environment can induce macrostrain and micro-strain in the tissue site 605, as well as remove contact layer polymer, at least one debriding agent, debris, exudate, and other fluids from the tissue site 605, which can be collected in container 115.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

In some embodiments, the methods may comprise providing cyclic therapy, alternately applying and venting negative pressure in the sealed environment 630, for example, via the therapy system 100. Thus, in some embodiments, the methods may further comprise venting the sealed environment 630. In some embodiments, negative pressure may be supplied to the sealed environment 630 until the pressure in the sealed environment 630 reaches a predetermined therapy pressure. Negative pressure may be supplied to the sealed environment 630 for any suitable amount of time, for example, at least about 10 minutes, at least about 30 minutes or less than about 60 minutes.

In some embodiments, negative pressure may be delivered to the tissue site 605 through the contact layer 140 or through the contact layer 140 and the debriding matrix 135. For example, the debriding matrix 135 may be porous, or may have perforations, slits, fenestrations or other fluid pathways through which fluid may be delivered to the tissue site 605. Additionally or alternatively, the debriding matrix 135 may be at least partially biodegraded or dissolved by one or more of exudate, instillation solution, and negative pressure, which can create fluid pathways.

In some embodiments, the sealed environment 630 may remain at the therapy pressure for a predetermined therapy period such as, for example, about 10 minutes, about 30 minutes or less than about 60 minutes. In other embodiments, the therapy period may be longer or shorter as needed to supply appropriate negative-pressure therapy to the tissue site 605.

Following the therapy period, the therapy system 100 may vent the environment 630. For example, the therapy system 100 may fluidly couple the sealed environment 630 to the atmosphere, allowing the sealed environment 630 to return to ambient pressure. In some embodiments, the therapy system 100 may vent the sealed environment 630 for about 1 minute, for example, by maintaining the sealed environment at ambient pressure. In other embodiments, the therapy system 100 may vent the sealed environment 630 for longer or shorter periods. After venting the sealed environment 630, the negative-pressure source 105 may begin another negative-pressure therapy cycle. In some embodiments, negative pressure may be supplied to the sealed environment 630 for about 1 minute and the sealed environment may be vented for about 1 minute.

In some embodiments, instillation therapy may be combined with negative-pressure therapy. For example, the solution source 150 may be fluidly coupled to the contact layer 140 through a second fluid conductor 645 and a second dressing interface 650 in some embodiments. Following a period of negative-pressure therapy, the therapy system 100 may operate the solution source 150 to provide fluid to the sealed environment 630. In some embodiments, the solution source 150 may provide fluid while the sealed environment 630 is vented. In other embodiments, the sealed environment 630 may not be vented, and the negative pressure in the sealed environment 630 may draw instillation fluid from the solution source 150 into the sealed environment 630.

In some embodiments, the solution source 150 may provide a volume of fluid to the sealed environment 630. In some embodiments, the volume of fluid may be the same as a volume of the sealed environment 630. In other embodiments, the volume of fluid may be smaller or larger than the sealed environment 630. Instilling solution into the sealed environment 630 can increase pressure above ambient pressure, for example to between about 0 mmHg and about 15 mmHg and, more specifically, about 5 mmHg In some embodiments, fluid provided by the solution source 150 may remain in the sealed environment 630 for a prescribed dwell time. In some embodiments, the dwell time may be about 5 minutes. In other embodiments, the dwell time may be longer or shorter as prescribed. For example, the dwell time may be zero.

At the conclusion of the dwell time, the negative-pressure source 105 may be operated to draw the instillation fluid into the container 115, completing a cycle of therapy. As the instillation fluid is removed from the sealed environment 630 with negative pressure, negative pressure may also be supplied to the sealed environment 630, starting another cycle of therapy.

In some examples, the tissue site 605 may include debris 655. For example, the debris 655 may comprise one or more of biofilms, necrotic tissue, lacerated tissue, devitalized tissue, contaminated tissue, damaged tissue, infected tissue, exudate, highly viscous exudate, and fibrinous slough. As shown in FIG. 6, the debris 655 may cover all or a portion of the tissue site 605.

The debris 655 may inhibit the efficacy of tissue treatment and slow the healing of the tissue site 605. For example, biofilms can comprise a microbial infection that can cover the tissue site 605 and impair healing of the tissue site 605. Biofilms can also lower the effectiveness of topical antibacterial treatments by preventing the topical treatments from reaching the tissue site 605.

Necrotic tissue may be dead tissue resulting from infection, toxins, or trauma that caused the tissue to die faster than the tissue can be removed by the normal body processes that regulate the removal of dead tissue. Sometimes, necrotic tissue may be in the form of slough, which may include viscous liquid mass of tissue. Generally, slough is produced by bacterial and fungal infections that stimulate an inflammatory response in the tissue. Slough may be a creamy yellow color and may also be referred to as pus. Necrotic tissue may also include eschar. Eschar may be a portion of necrotic tissue that has become dehydrated and hardened. Eschar may be the result of a burn injury, gangrene, ulcers, fungal infections, spider bites, or anthrax, and can be difficult to remove.

Once positioned adjacent to the tissue site 605, at least a portion of the debriding matrix 135 may biodegrade or dissolve and continue to biodegrade or dissolve, for example, throughout installation therapy and/or negative pressure therapy. One or more debriding agents may contact the tissue site 605 and advantageously debride, for example, through enzymatic debridement, at least a portion of the tissue site 605 including debris 655 present therein. In some embodiments, debridement may only comprise enzymatic debridement.

In some embodiments, the debris 655 can be removed, for example, from a surface of the tissue site 605, during dressing changes. Advantageously, time between dressing changes can be increased, for example, by controlling the rate at which the debriding matrix biodegrades or dissolves. For example, the wound dressing may remain adjacent to a tissue site for greater than 1 day, greater than 3, greater than 5 days, or greater than 7 days, before a dressing change. In some embodiments, the wound dressing may remain adjacent to a tissue for about 1 to 7 days or about 3 to 5 days. Further, use of instillation therapy during these intervals between dressing changes can advantageously remove at least a portion of a debriding agent from the tissue site so that toxicity to the tissue site can be minimized.

In some embodiments, the cover 145 may be removed from contact layer 140 and disrupted debris 655 may be removed by wiping away the debris 655. In other embodiments, the contact layer 140 may disrupt the debris 655 so that the debris 655 can be removed by negative pressure. In some embodiments, the methods described herein, for example using the therapy system 100, may be used in conjunction with other tissue removal and debridement techniques. For example, further mechanical and/or enzymatic debridement process may be used to remove further portions of the debris 655, for example, before positioning of the wound dressing 110 and/or after supplying negative pressure and/or fluid to the tissue site 605. Additionally or alternatively, sharp debridement may also be used as necessary for removal at least a portion of the debris 655, for example, before positioning of the wound dressing 110 and/or after supplying negative pressure and/or fluid to the tissue site 605. Sharp debridement may include, but is not limited to the use of a scalpel, scissor or other sharp instrument in debriding a tissue site.

In some embodiments, the therapy system 100 can provide mechanical movement and debriding agents in combination with negative pressure, instillation solution, or both to solubilize, debride, and/or remove the debris 655. Thus, mechanical debridement and enzymatic debridement may be provided in combination. In some embodiments, cyclical application of instillation therapy and negative pressure therapy may cause the contact layer 140 to float and change position relative to the debris 655. For example, negative pressure may be applied to the sealed environment 630 during a negative-pressure therapy cycle. Following the conclusion of the negative-pressure therapy cycle, instillation fluid may be supplied during the instillation therapy cycle. The instillation fluid may cause the contact layer 140 to float relative to the debris 655. The position change may cause the contact layer 140 to engage a slightly different portion of the debris 655 during the next negative-pressure therapy cycle, aiding disruption of the debris 655.

Additionally or alternatively, in some embodiments, negative pressure can cause the contact layer 140 contract, applying a lateral force on the debris 655. The lateral force may be related to a compressive force generated by applying negative pressure to the sealed environment 630. For example, the lateral force may be proportional to a product of a therapy pressure (TP) in the sealed environment 630, the compressibility factor (CF) of the contact layer 140, and a surface area (A) the first surface 210 of the contact layer 140. The lateral force can be approximated as the product of TP*CF*A. In some embodiments, the therapy pressure TP is measured in $N/m^2$, the compressibility factor (CF) is dimensionless, the area (A) is measured in $m^2$, and the lateral force is measured in Newtons (N). The compressibility factor (CF) resulting from the application of negative pressure to the contact layer 140 may be, for example, a dimensionless number that is proportional to the product of the void space percentage (VS) of the contact layer 140, the firmness factor (FF) of the contact layer 140, the strut angle (SA) of the contact layer 140, and the shape factor (SF) of the perforations 205 in the contact layer 140. The relationship can be expressed as (CF) a (VS*FF*sin (SA)*SF). In some embodiments, the relationships may not precisely describe the lateral forces due to losses from the transfer of the force from the contact layer 140 to the tissue site 605. For example, the modulus and stretching of the cover 145, the modulus of the tissue site 605, slippage of the cover 145 over the tissue site 605, and friction between the contact layer 140 and the tissue site 605 may cause the actual value of the lateral force to be less than the calculated value of the lateral force.

FIG. 7 is a view of the contact layer 140 of FIG. 3 contracting under negative pressure, illustrating additional details that may be associated with mechanical disruption of the debris 655 in some embodiments. If the contact layer 140 is subjected to negative pressure, the perforations 205 may contract, which can disrupt the debris 655. For example, the edges of the perforations 205 may form cutting edges that can disrupt the debris 655. In some embodiments, the cutting edges may be defined by the perimeter 410 of each of the perforations 205. If negative pressure is removed, for example, by venting the negative pressure, the contact layer 140 can expand back to a relaxed position. If the contact layer 140 is cycled between the contracted and relaxed positions, the contact layer 140 may mechanically disrupt the debris 655 further. In some embodiments, the negative pressure applied by the negative-pressure source 105 may be cycled rapidly. For example, negative pressure may be supplied for a few seconds and then vented for a few seconds, causing a pulsation of negative pressure in the sealed environment 630. The pulsation of the negative pressure can pulse the nodules 805, which can cause further disruption of the debris 655. Such contraction of the contact layer 140 and perforations 205 in combination with the action of the one or more debriding agents at the tissue site 605 can not only advantageously allow for increased debridement at the tissue site 605 but also advantageously result in co-action or synergy in debriding the tissue site 605 and debris 655.

Contraction can refer to both vertical contraction and lateral contraction. The material, the void space percentage, the perforation shape factor, the firmness factor, the dimensions of the perforations 205, and the strut angle may influence or control the direction of contraction. For example, in some embodiments, one or more of the void space percentage, the perforation shape factor, or the strut angle can cause the contact layer 140 to contract along the second orientation line 310 perpendicular to the first orientation line 305 as shown in FIG. 7. If the contact layer 140 is positioned on the tissue site 605, the contact layer 140 may contract in the direction 705 toward the first orientation line 305. In some embodiments, the perforations 205 may be circular, the strut angle may be approximately 37°, the void space percentage may be about 54%, the firmness factor may be about 5, the shape factor may be about 1, and the diameter may be about 5 millimeters. If the contact layer 140 is subjected to a negative pressure of about −125 mmHg, the contact layer 140 can assert a lateral force in the direction 705 of approximately 11.9 N. If the diameter of the perforations 205 is increased to about 20 millimeters, the void space percentage changed to about 52%, the strut angle changed to about 52°, and the perforation shape factor and the firmness factor remain the same, the lateral force can be decreased to about 6.5 N.

Additionally or alternatively, in some embodiments, channeling negative pressure in the sealed environment 630, for example, through the perforations 205, can cause concentrated stresses on the debris 655 adjacent to the perforations 205. The forces applied to the debris 655 can be a function of the negative pressure supplied to the sealed environment 630 and the cross-sectional area of each of the perforations 205. For example, if the negative pressure is about 125 mmHg and the perforations 205 have a diameter of about 5 millimeters, the force applied at each of the perforations 205 may be about 0.07 lbs. If the diameter of each of the perforations is increased to about 8 millimeters, the force applied at each of the perforations 205 can increase up to 6 times. Generally, the relationship between the dimensions of each of the perforations 205 and the applied force at each of the perforations 205 is not linear and can increase exponentially with an increase in diameter. In some embodiments, healthy tissue adjacent to the tissue site 605 may not be substantially disrupted during the method.

Figure 8:
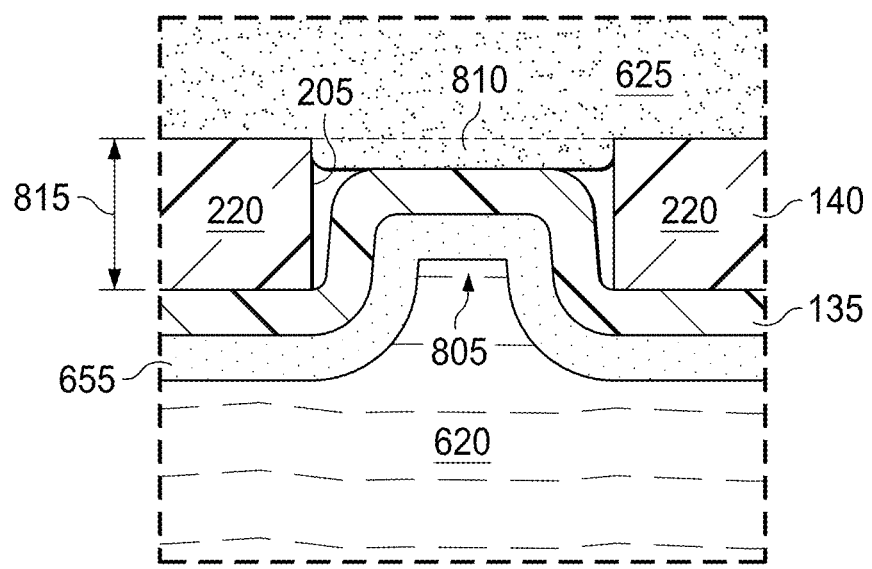
FIG. 8 is a detail view of the therapy system of FIG. 6, illustrating additional details that may be associated with some embodiments of a contact layer and an optional filler.

FIG. 8 is a detail view of the therapy system 100 of FIG. 6, illustrating additional details that may be associated with the contact layer 140 and the optional filler 625 under negative pressure as used in the methods described herein. As illustrated in FIG. 8, concentrated stresses on the debris 655 adjacent to the perforations 205, for example, by channeling negative pressure through the perforations 205, can generate macro-deformations of the debris 655 and the subcutaneous tissue 620, which can draw nodules 805 of the subcutaneous tissue 620 having debris 655 thereon into the perforations 205. In some embodiments, the methods may comprise debriding at least a portion of the debris 655 on the nodules 805. Portions of the filler 625 may also be drawn into the perforations 205 to form bosses 810. The bosses 810 may have a shape that corresponds to a shape of the perforations 205. The size of the bosses 810 may be dependent, for example, on the magnitude of negative pressure in the sealed environment 630, the dimensions of the perforations 205, and the firmness factor of the filler 625. At least a portion of the debriding matrix 135, which may be at least partially biodegraded or dissolved, may be present adjacent to at least a portion of the debris 655.

In some embodiments, supplying negative pressure to the sealed environment 630 may create macro-pressure points in portions of the debris 655 and the subcutaneous tissue 620 that are in contact with a tissue-facing surface of the contact layer 140, causing tissue puckering and nodules 805 in the debris 655 and the subcutaneous tissue 620.

A height of the nodules 805 over the surrounding tissue may be controlled or limited to maximize disruption of debris 655 and minimize damage to subcutaneous tissue 620 or other desired tissue. Generally, negative pressure in the sealed environment 630 can exert a force that is proportional to the area over which the pressure is applied. At the perforations 205, the force may be concentrated as the resistance to the application of the pressure is less than in the walls 220 of the contact layer 140. In response to the force generated by the pressure at the perforations 205, the debris 655 and the subcutaneous tissue 620 that forms the nodules 805 may be drawn into and through the perforations 205 until the force applied by the pressure is equalized by the reactive force of the debris 655 and the subcutaneous tissue 620. In some embodiments, a thickness 815 of the contact layer 140 may be selected to limit the height of the nodules 805 over the surrounding tissue. Additionally or alternatively, in some embodiments, the filler 625 may limit the height of the nodules 805 to the thickness 815 of the contact layer 140 under negative pressure if the contact layer 140 is compressible. In other embodiments, the bosses 810 may limit the height of the nodules 805 to a height that is less than the thickness 815 of the contact layer 140. The firmness factor of the filler 625 can be selected to control the depth of the bosses 810 into the perforations 205. The height of the nodules 805 can be limited to the difference between the thickness 815 and the depth of the bosses 810. In some embodiments, the depth of the bosses 810 can vary from zero to several millimeters. For example, the thickness 815 of the contact layer 140 may be about 7 millimeters in some embodiments, and the bosses 810 may have a height between about 4 millimeters to about 5 millimeters, limiting the height of the nodules to about 2 millimeters to about 3 millimeters. By controlling the height of the nodules 805, the aggressiveness of disruption to the debris 655 and tearing can be controlled.

In some embodiments, the contact layer 140 may have first thickness at ambient pressure, and the method may further comprise compressing the contact layer 140 to a second thickness that may be less than the first thickness. Nodules 805 may be formed with a height no greater than the second thickness. In some embodiments, the first thickness may be at least about 6 mm, at least about 8 mm or from about 6 mm to about 10 mm. In some embodiments, the second thickness may be at least about 2 mm, at least about 3 mm or from about 2 mm to about 4 mm.

In some embodiments, the height of the nodules 805 can also be controlled by controlling compressibility of the contact layer 140. For example, if the contact layer 140 is formed from compressed foam, the firmness factor of the contact layer 140 may be higher than uncompressed foam. The thickness 815 of the contact layer 140 may be about 8 millimeters in some embodiments of compressed foam. Negative pressure of between about −50 mmHg and about −350 mmHg, between about −100 mm Hg and about −250 mmHg and, more specifically, about −125 mmHg in the sealed environment 630 may reduce the thickness 815 of the contact layer 140 from about 8 millimeters to about 3 millimeters. If filler 625 is placed over the contact layer 140, the height of the nodules 805 may be limited to about 3 millimeters. By controlling the height of the nodules 805, the forces applied to the debris 655 can be adjusted and the degree that the debris 655 is stretched can be varied. In some embodiments, cyclic application of negative pressure may lift the debris 655 and other particulates off of the surrounding tissue, operating in a piston-like manner to move the debris 655 toward the filler 625 and out of the sealed environment 630. The application and removal of negative pressure to the sealed environment 630 can also rupture the nodules 805 in some examples.

In some embodiments, dimensions of the perforations 205 may be selected to permit flow of particulates through the perforations 205. In some embodiments, for example, the effective diameter of the perforations 205 may be selected based on an anticipated size of solubilized debris to be lifted from a tissue site. Dimensions may also be selected to allow larger debris and block smaller debris. In some examples, some or all of the debris 655 may be drawn through the perforations 205 and collected in the container 115. Optionally, the size of the perforations 205 may differ on successive applications of the wound dressing 110. For example, the dimensions of the perforations 205 may be decreased as the size of the debris 655 decreases. Sequentially decreasing size of the perforations 205 may also aid in fine tuning a level of tissue disruption to the debris 655 during the treatment of the tissue site 605.

The dimensions of the perforations 205 can also influence fluid movement in the contact layer 140 and the wound dressing 110. For example, the contact layer 140 can channel fluid in the wound dressing 110 toward the perforations 205 to aid in the disruption of the debris 655 on the tissue site 605. Variation of the dimensions of the perforations 205 can vary how fluid is moved through the wound dressing 110 with respect to both the removal of fluid and the application of negative pressure.

Figure 9:
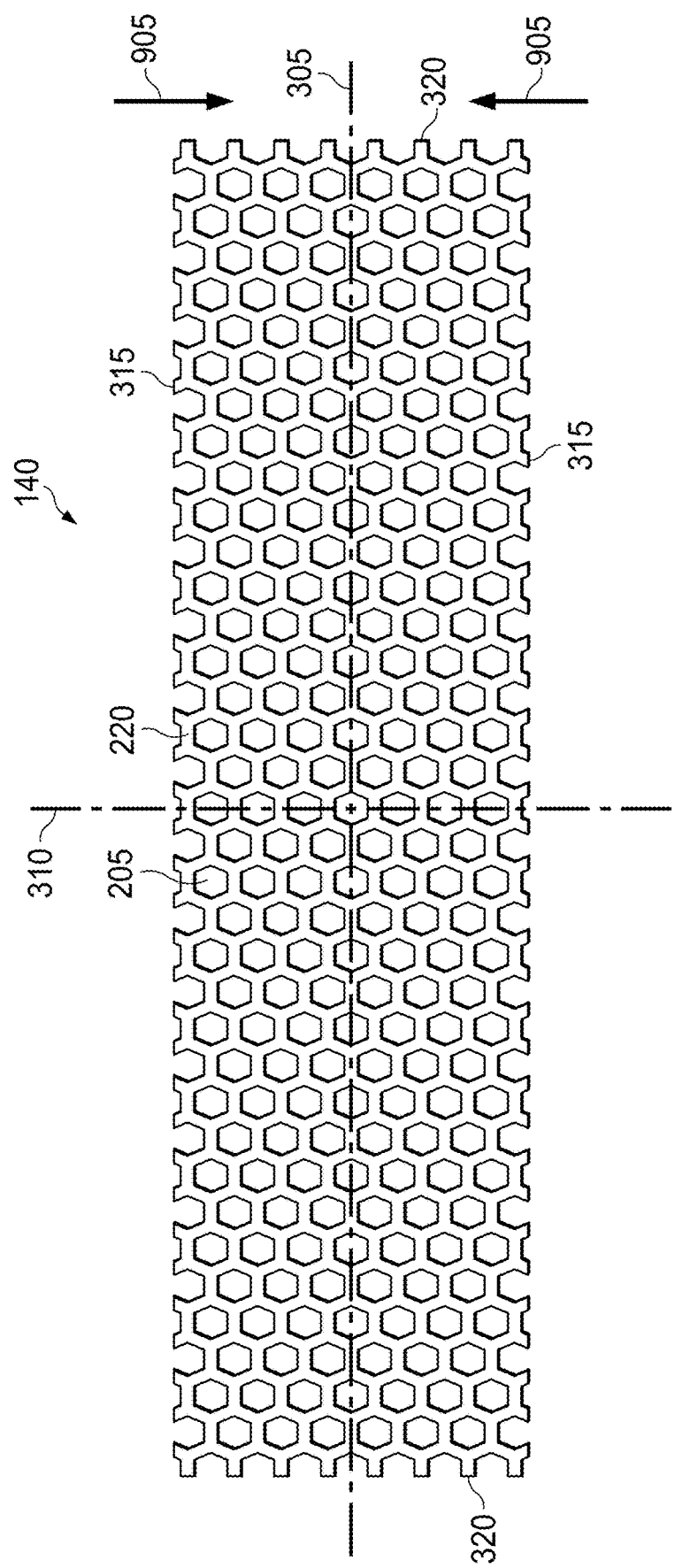
FIG. 9 is a plan view of another example of a contact layer, illustrating additional details that may be associated with some embodiments.
Figure 10:
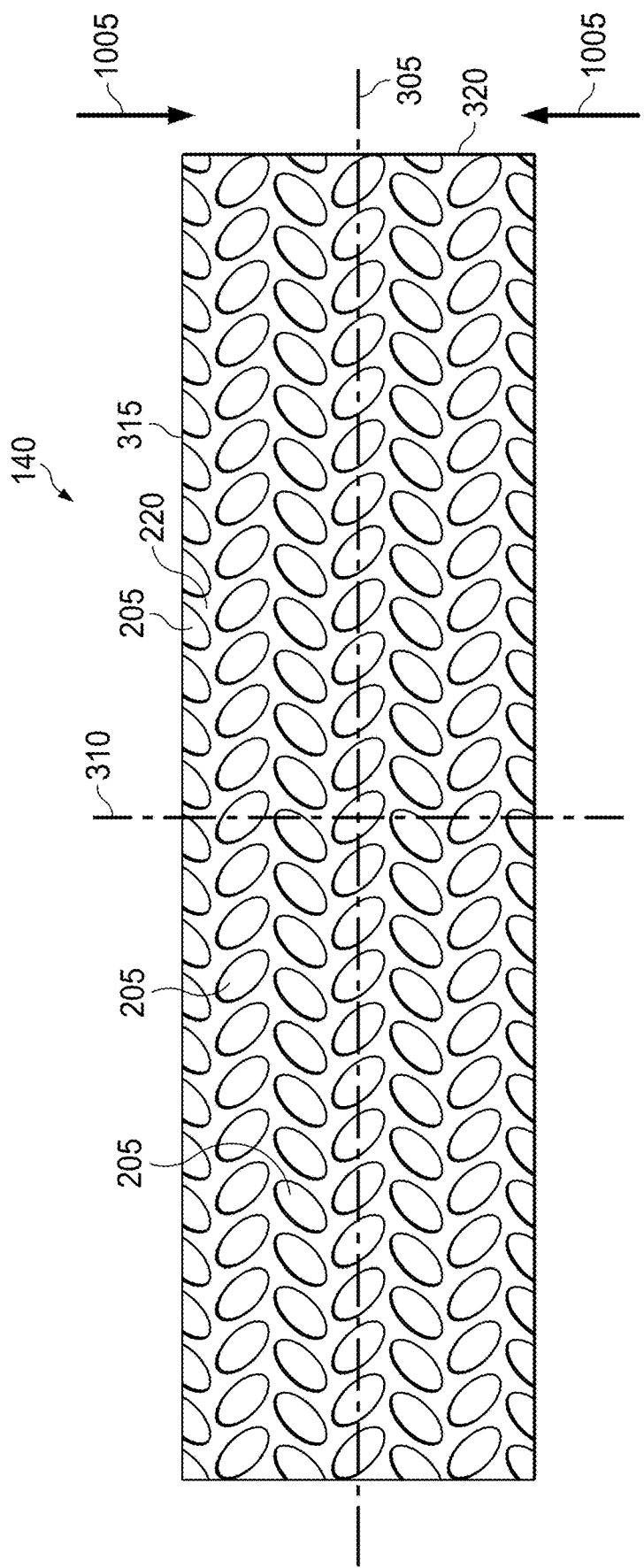
FIG. 10 is a plan view of another example of a contact layer, illustrating additional details that may be associated with some embodiments.
Figure 11:
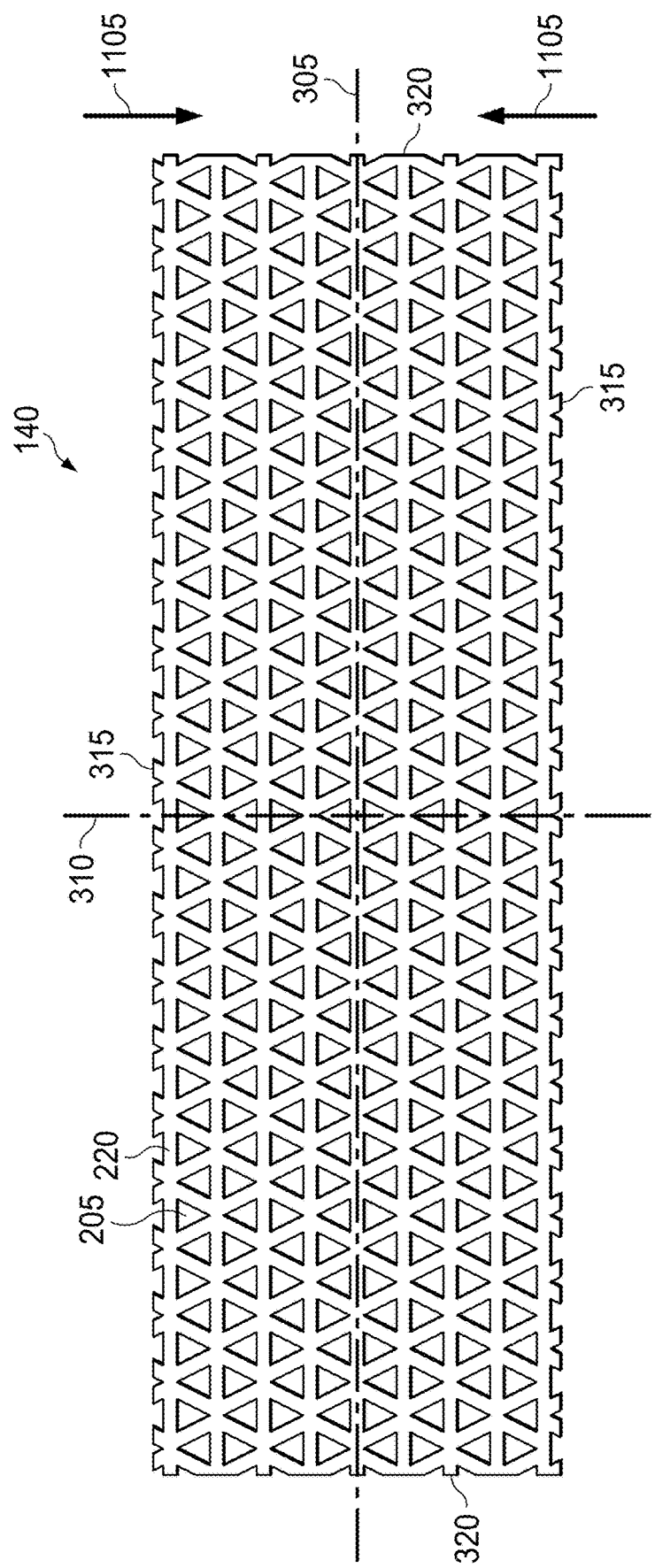
FIG. 11 is a plan view of another example of a contact layer, illustrating additional details that may be associated with some embodiments.

The shape of the perforations 205 may vary in different embodiments of the contact layer 140 to vary the concentration of stresses. For example, FIG. 9 is a plan view of another embodiment of the contact layer 140, illustrating additional details in which the perforations 205 have a hexagonal cross-section and a lateral force 905. Stresses on the debris 655 may be focused at the vertices of the perforations 205 in the example of FIG. 9. Suitable characteristics of the contact layer 140 of FIG. 9 may include a strut angle of approximately 66°, a void space percentage of about 55%, a firmness factor of about 5, a perforation shape factor of about 1.07, and an effective diameter of about 5 millimeters. If the contact layer 140 of FIG. 9 is subjected to a negative pressure of about −125 mmHg, the lateral force 905 of the contact layer 140 may be about 13.3 N. If the effective diameter of the perforations 205 is increased to 10 millimeters, the lateral force 905 may be decreased to about 7.5 N. FIG. 10 is a plan view of another example of the contact layer 140, illustrating additional details in which the perforations 205 have an elliptical or oval cross-section and a lateral force 1005. FIG. 11 is a plan view of another example of the contact layer 140, illustrating additional details in which the perforations 205 have a triangular cross-section and a lateral force 1105.

Figure 12:
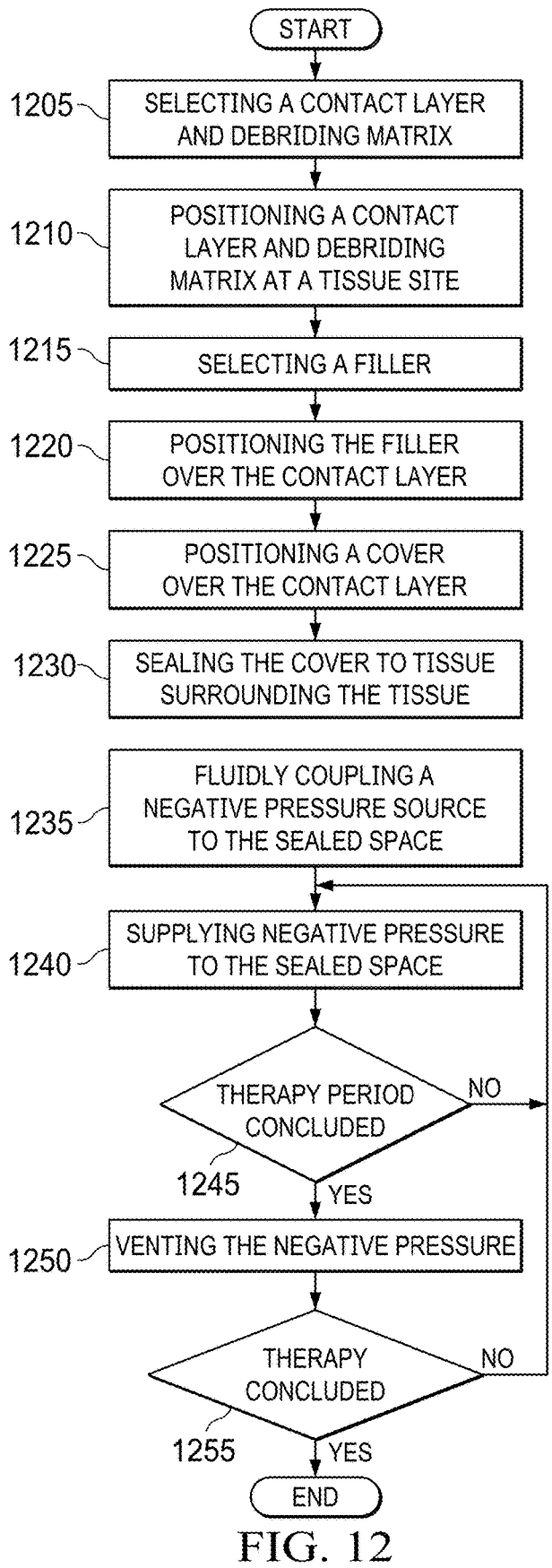
FIG. 12 is a flow chart illustrating exemplary operations that can be associated with some embodiments of the therapy system of FIG. 1.

FIG. 12 is a flow chart illustrating exemplary operations that can be associated with some embodiments of the therapy system 100. One or more operations may be implemented by a controller, such as the controller 120, configured to execute the operations. At block 1205, the wound dressing 110 including the contact layer 140 and/or debriding matrix 135 may be selected for use on the tissue site 605. At block 1210, the contact layer 140 and the debriding matrix 135, separately or together, can be positioned at a tissue site, such as the tissue site 605. At block 1215, a filler may be selected for use on the tissue site. At block 1220, the selected filler can be positioned over the contact layer 140. For example, the filler 625 can be positioned over the contact layer 140. At block 1225, a cover may be positioned over the filler 625, the contact layer 140, and the tissue site 605, and at block 1230, the cover can be sealed to tissue surrounding a tissue site. For example, the cover 145 can be positioned over the tissue site 605 and sealed to tissue surrounding the tissue site 605.

At block 1235, a negative pressure source can be fluidly coupled to a sealed space formed by the cover. For example, the negative-pressure source 105 can be fluidly coupled to the sealed environment 630 formed by the cover 145. At block 1240, the negative-pressure source can supply negative pressure to the sealed space. For example, a controller can actuate the negative-pressure source 105 to supply negative-pressure to the sealed environment 630 for a negative-pressure therapy period.

At block 1245, the controller can determine if the negative-pressure therapy period has concluded. For example, a controller of the negative-pressure source 105 can determine if a timer, started when the negative-pressure source was actuated to supply negative pressure, has reached a predetermined time. The predetermined time may be based on an expected timer interval for negative-pressure therapy of the predetermined time may be a time period selected by a user. At block 1245, if the timer has not expired, the method can continue on the NO path to block 1240, where the controller of the negative-pressure source can continue supplying negative pressure to the sealed space.

At block 1245, if the timer has expired, the method can continue on the YES path to block 1250, where the controller of the negative-pressure source can vent the negative pressure in the sealed space to the ambient environment. For example, the controller of the negative-pressure source 105 can vent the sealed environment 630 to the ambient environment.

At block 1255, the method determines if therapy has concluded. For example, the controller of the negative-pressure source 105 can determine if a predetermined number of supply and vent cycles has been completed. The predetermined number of supply and vent cycles can be a standard number of cycles for therapy or can be a number of cycles entered in by a user. If therapy has not concluded, the method can continue on the NO path to block 1240, where the negative-pressure source can be operated to supply negative pressure to the sealed space. If therapy has concluded, the method can continue on the YES path, where the method ends.

Figure 13:
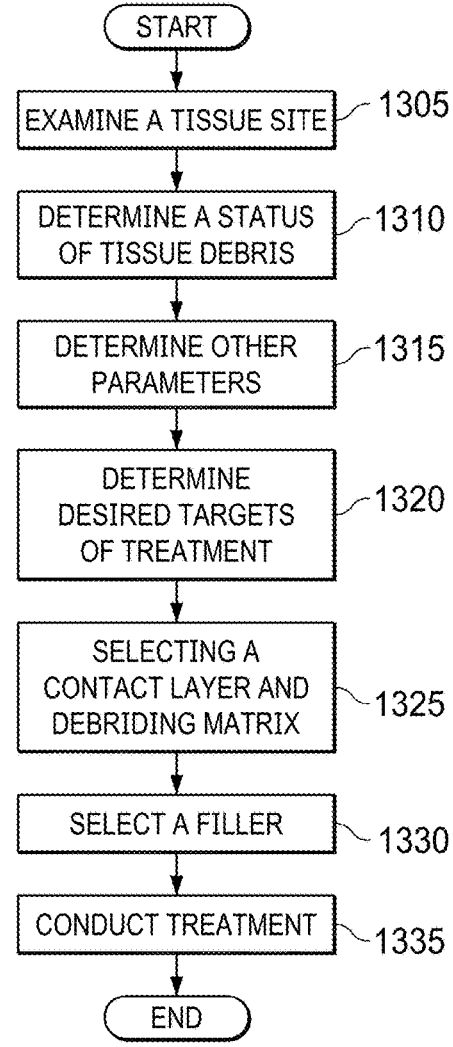
FIG. 13 is a flow chart illustrating exemplary operations that can be associated with some embodiments of the therapy system of FIG. 1.

FIG. 13 is a flow chart illustrating exemplary operations that can be associated with some embodiments of the therapy system 100. One or more operations may be implemented by a controller, such as the controller 120, configured to execute the operations. Operations may also be performed by a user, such as a clinician. At block 1305, a user may examine a tissue site. For example, a clinician may examine the tissue site 605.

At block 1310, a status of the debris of the tissue site may be determined. For example, a clinician may determine that the debris 655 covers the tissue site 605. The status can also include one or more of: a thickness of the debris 655, a consistency of the debris 655, a color of the debris 655, and a moisture level of the debris 655. For example, a clinician may determine that the debris 655 at the tissue site 605 may have a thin, thick, runny, solid, rough, firm, smooth, heavy, or light consistency. The clinician may determine that the debris 655 at the tissue site 605 has a black, red, brown, green, yellow, gray, or other color that is indicative of a state of infection of the tissue site 605. The clinician can also evaluate the moisture condition of the debris 655, for example on a scale ranging from no presence of liquid to saturated. In some embodiments, the determination of a moisture level can aid a clinician in understanding how much exudate is present in the tissue site 605.

At block 1315, other parameters influencing treatment can be evaluated. For example, a clinician can determine a patient's pain tolerance, environment, preference, age, co-morbidities, quality of life, caregiver resources, and caregiver skills.

At block 1320, based on the information determined at block 1310 and block 1315, desired targets for treatment of debris at a tissue site can be determined. For example, a clinician can determine if the debris 655 comprises necrotic tissue, eschar, impaired tissue, other sources of infection, exudate, slough including hyperkeratosis, pus, foreign bodies, biofilm, or other types of bioburden. A clinician can also determine if treatment will reduce unpleasant odors, excess moisture, and the risk of infection of the debris 655 and the tissue site 605.

At block 1325, in response to the determination of the desired targets for treatment of the debris at the tissue site, wound dressing including a contact layer and/or a debriding matrix can be selected. For example, a contact layer based on a firmness factor, a thickness, a through-hole shape, a through-hole size, and an array pattern to achieve the desired targets for treatment. For example, a polymer and optional thickening, drying and slow release agents may be selected based on desired dissolution rate of the debriding matrix and type of wound, wound exudate and/or bacteria present. For example, one or more debriding agents may be selected based on the type of wound, wound exudate, and/or bacteria present. For example, a clinician may select a contact layer having cylindrical perforations to permit the flow of the debris 655 having a yellowish color, a thick consistency, and a high moisture level. The clinician can further select a contact layer with perforations having a diameter greater than a size of the largest solubilized debris in a tissue site. In other embodiments, the clinician may select a contact layer having triangular perforations, for example, if the debris is rough, black, and has low moisture content.

At block 1330, in response to the determination of the desired targets for treatment of the debris at the tissue site, an optional filler may be selected. For example, the clinician can select a filler based on a firmness factor and a thickness. Generally, the thickness of the filler may be selected to fill a tissue site. The clinician may also select the firmness factor of the filler to limit the height of the nodules 805. For example, if the debris 655 is thinner than the contact layer 140, has a runny consistency, and has a smooth surface, the clinician may select a filler having a low firmness factor. A lower firmness factor of the filler may permit the bosses 810 to have a larger height than a filler having a high firmness factor, thereby decreasing the height of the nodules 805. At block 1335, a tissue site can be treated with the wound dressing. For example, the clinician may conduct treatment with the contact layer 140 and the therapy system 100.

III. Kit

In some embodiments, a contact layer, such as the contact layer 140, and a debriding matrix, such as the debriding matrix 135, may be provided as components of a wound dressing kit, where the contact layer and the debriding matrix may be separate or together. In some embodiments, the contact layer may be provided without any of the perforations, such as perforations 205, and the kit may include a punch that can be used to form the perforations in the contact layer. In some embodiments, the debriding matrix may be provided without any perforations. The kit can provide a user, such as a clinician, the ability to customize the contact layer and/or the debriding matrix to a particular tissue site so that, for example, the perforations disrupting only the debris, such as debris 655, and not healthy tissue that may be near or surround the debris. In some embodiments, a kit may optionally include more or more fillers of different sizes, for example the filler 625 may be provided. For example, a first filler layer may having a thickness of between about 5 millimeters and about 15 millimeters and, more specifically, about 8 millimeters. A second filler layer may have a thickness between about 10 millimeters and about 20 millimeters and, more specifically, about 16 millimeters. One or both of the filler layers may be selected as needed to fill a tissue site.

The systems, apparatuses, methods and kits described herein may provide significant advantages. For example, combining the mechanical action of a contractible contact layer with hydrating and flushing action of instillation and negative-pressure therapy can significantly reduce or eliminate pain associated with debridement of a tissue site and can allow for longer time intervals in between dressing changes. A wound dressing such as the wound dressing 110 may also require less monitoring from a clinician or other attendant as compared to other mechanical debridement processes and enzymatic debridement processes. In addition, the contact layer 140 may not become blocked by removed necrotic tissue as may occur during autolytic debridement of a tissue site. Furthermore, the contact layer 140 and/or the debriding matrix 135 can aid in removal of necrosis, eschar, impaired tissue, sources of infection, exudate, slough including hyperkeratosis, pus, foreign bodies, debris, and other types of bioburden or barriers to healing. The contact layer 140 and/or the debriding matrix 135 can also decrease odor, excess moisture, and the risk of infection while stimulating edges of a tissue site and epithelialization. Some embodiments of the wound dressing such as the wound dressing 110 can also provide improved removal of thick exudate, allow for earlier placement of instillation and negative-pressure therapy devices, may limit or prevent the use of other debridement processes, and can be used on tissue sites that are difficult to debride.

The contact layer and/or the debriding matrix can also be used with other layers or components without the perforations. For example, the contact layer 140 may be provided and can be cut to fit debris at a tissue site, and other layers or components may be placed over remaining areas of the tissue site. Similarly, other layers or components may be placed between the contact layer and the debriding matrix or between the tissue site and the wound dressing where no disruption is desired.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the wound dressing 110, the container 115, or both may be eliminated or separated from other components for manufacture or sale. In other example configurations, the controller 120 may also be manufactured, configured, assembled, or sold independently of other components.

EXAMPLES

The benefits associated with the wound dressings, systems, and methods are further demonstrated by the following, non-limiting Examples. These Examples may demonstrate one or more features associated with some embodiments of the wound dressings, systems, and methods.

Example 1

Solubility Testing of Polysaccharide Matrix

A 1 mm layer of a polysaccharide based matrix (commercial source of 16 ounce ripe raspberries, 10% Pectin in water, blended and baked until hardened) was applied to a surface of a foam (V.A.C. VERAFLO CLEANSE CHOICE™ dressing) contact layer having perforations therein to form a Dressing 1. FIG. 14a shows a first surface (bottom view) of the Dressing 1 having the polysaccharide based matrix layer thereon, where the polysaccharide based matrix covered the perforations in the foam contact layer. FIG. 14b shows a second surface (top view) opposing the first surface of the Dressing 1 with perforations therein having no polysaccharide based matrix on the second surface. FIG. 14c shows a side view of the Dressing 1. Dressing 1 underwent a first instillation cycle (V.A.C. ULTA™ therapy unit with V.A.C. VERAFLO™ therapy) with saline (1 minute dwell cycle), followed by a first NPWT cycle (3 minute cycle), followed by a second instillation cycle with saline, and followed by a second NPWT cycle. FIGS. 15a and 15b show Dressing 1 before the instillation and NPWT cycles. FIG. 15c shows the first surface of Dressing 1 after the first instillation cycle. FIG. 15d shows the first surface of Dressing 1 after the first NPWT cycle. FIG. 15e shows the first surface of Dressing 1 after the second instillation cycle. FIG. 15f shows the first surface of Dressing 1 after the second NPWT cycle. As shown in FIGS. 15a-15f, the polysaccharide based matrix dissolved from the foam contact layer during the course of therapy as evidenced by the unobscured perforations Example 2

Comparison of Debridement Solutions on Simulated Eschar

Figures 16A, 16B:
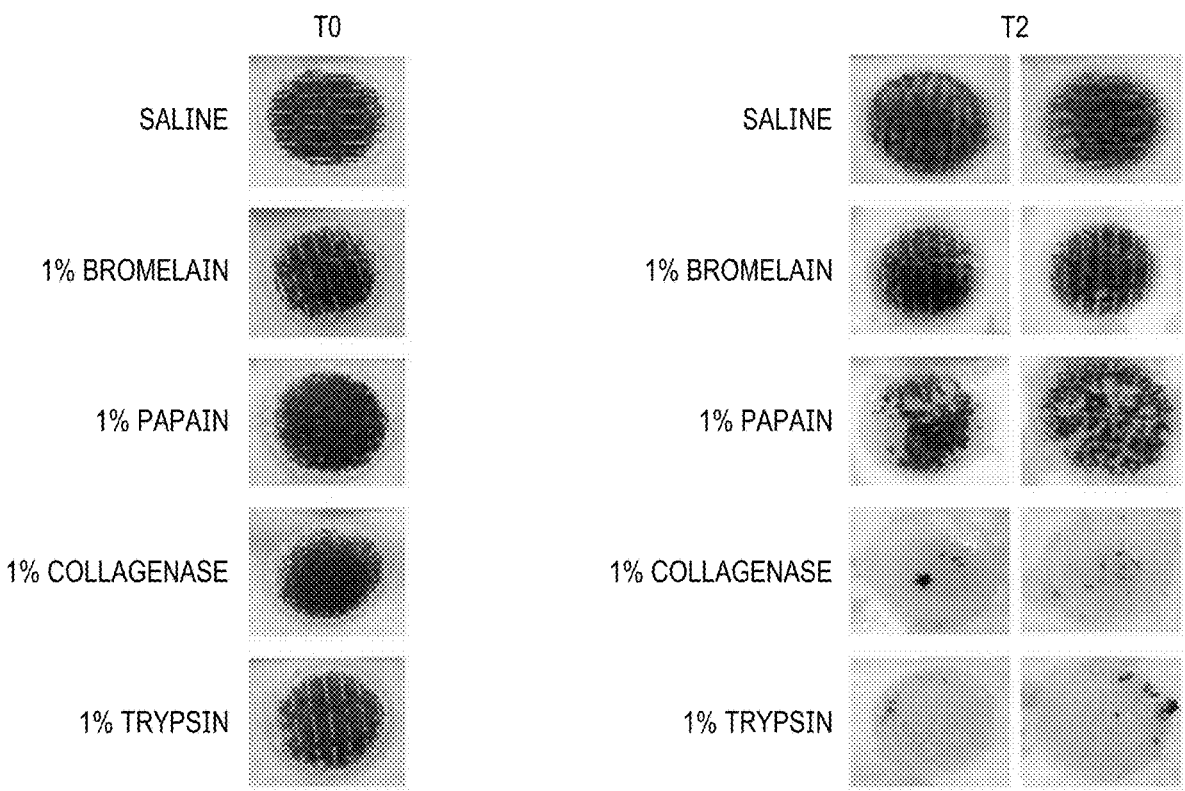
FIG. 16a is a series of photographs of simulated eschar having applied thereon phosphate-buffered saline (PBS) and the following four debridement solutions, 1% bromelain, 1% papain, 1% collagenase, and 1% trypsin, at zero hours (T0).
FIG. 16b is a series of photographs of the simulated eschar having applied thereon PBS and the following four debridement solutions, 1% bromelain, 1% papain, 1% collagenase, and 1% trypsin, at two hours (T2).
Figure 16C:
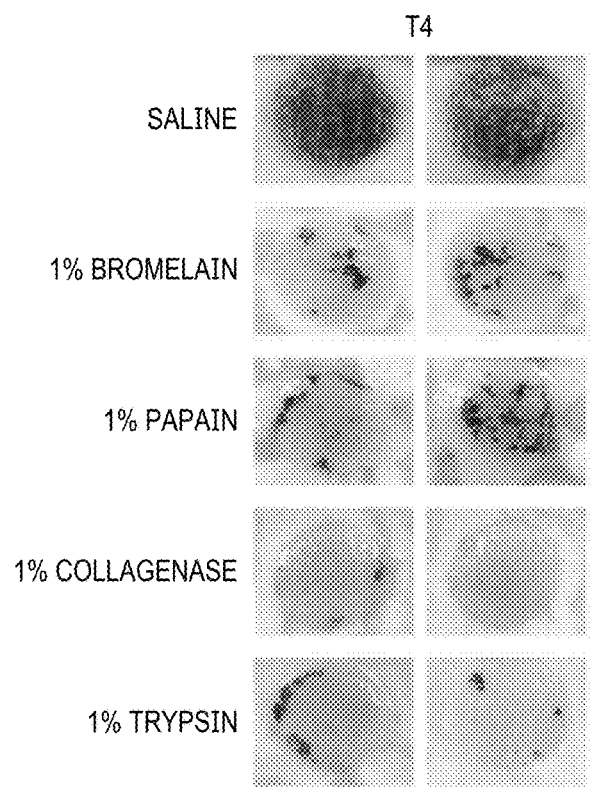
FIG. 16c is a series of photographs of the simulated eschar having applied thereon PBS and the following four debridement solutions, 1% bromelain, 1% papain, 1% collagenase, and 1% trypsin, at four hours (T4).

The following four different debridement solutions were prepared: 1% bromelain, 1% papain, 1% collagenase, and 1% trypsin (enzymes were obtained from commercial sources and dissolved at 0.1 g/10 mL in saline). These four debridement solutions along with phosphate-buffered saline (PBS) were applied to simulated eschar (burned pig skin). Degree of debridement for the four debridement solutions and PBS was captured via photographs at three different time points: zero hours (T0), 2 hours (T2) and 4 hours (T4). The results for the four debridement solutions and PBS are shown in FIGS. 16a, 16b and 16c for T0, T2, and T4, respectively.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A wound dressing comprising:
   a contact layer formed from a foam material having a plurality of pores, the contact layer having a first surface and a second surface opposite the first surface and configured to be positioned adjacent a tissue site;
   a plurality of perforations extending through the contact layer from the first surface to a second surface, the plurality of perforations forming walls in the contact layer; and
   a debriding matrix comprising a solid sheet formed from a polymer and at least one debriding agent, wherein the debriding matrix is removably adhered to at least a portion of the second surface of the contact layer and covers the plurality of perforations.

2. The wound dressing of claim 1, wherein one or more of the following are satisfied:
   at least a portion of the plurality of perforations are not covered with the debriding matrix;
   the debriding matrix has a thickness of 1.0 mm to 10 mm.

3. The wound dressing of claim 1, wherein the debriding matrix has a soluble solid composition in an aqueous solution having a pH from 2 to 10 of at least 10%.

4. The wound dressing claim 1, wherein the debriding matrix comprises fluid pathways.

5. The wound dressing of claim 1, wherein the debriding agent is active at a pH of 2 to 12.

6. The wound dressing of claim 1, wherein the debriding agent is present in the debriding matrix in 0.25 United States Pharmacopeia 9"USP") units to 1,000 USP units.

7. The wound dressing of claim 1, wherein the debriding agent is selected from the group consisting of papain, urea, streptokinase, streptodornase, trypsin, collagenase, fibrinolysin, fibrinolysin with deoxyribonuclease, bromelain and a combination thereof.

8. The wound dressing of claim 1, wherein the polymer is a polysaccharide, a protein, a vegetable gum, or a combination thereof.

9. The wound dressing of claim 1, wherein the debriding matrix further comprises a drying agent selected from the group consisting of silica gel, magnesium aluminum silicate, calcium oxide, calcium sulfate, a sulfonate and a combination thereof; a thickening agent selected from the group consisting of glycerol, glycerin, a carbomer, polyethylene glycol and a combination thereof; and/or oxidized regenerated cellulose (ORC).

10. The wound dressing of claim 1, wherein the plurality of perforations have an average diameter of 5.0 mm to 20 mm.

11. The wound dressing of claim 1, wherein the plurality of perforations are present in an array comprising two or more parallel rows.

12. The wound dressing of claim 1, wherein at least a portion of the perforations have a depth less than a thickness of the contact layer, and wherein the contact layer has a thickness of 5.0 mm to 20 mm.

13. The wound dressing of claim 1, wherein the walls of the perforations have a substantially smooth surface between the first surface of the contact layer and the second surface of the contact layer.

14. The wound dressing of claim 1, wherein the contact layer has a void space percentage of 40% to 75% and is formed from a compressed foam, a felted foam, a 3D spacer fabric, a thermoplastic elastomer or a thermoplastic polyurethane.

15. A method for debriding a tissue site, the method comprising:
- positioning the wound dressing of claim 1 adjacent to the tissue site;
- positioning a cover over the contact layer;
- sealing the cover to tissue surrounding the tissue site to form a sealed environment enclosing the wound dressing;
- fluidly coupling a negative-pressure source to the wound dressing; and
- supplying negative pressure to the wound dressing to draw tissue into the perforations to form nodules.

16. The method of claim 15, further comprising dissolving at least a portion of the debriding matrix at the tissue site.

17. The method of claim 16, further comprising:
- positioning a filler adjacent to the contact layer, opposite the tissue site;
- drawing portions of the filler into the plurality of perforations of the contact layer to form bosses; and
- contacting a top of the nodules to limit a height of the nodules.

18. The method of claim 15, wherein the contact layer has a first thickness at ambient pressure and the method further comprises:
- compressing the contact layer to a second thickness that is less than the first thickness; and
- forming nodules with a height no greater than the second thickness.

19. The method of claim 18, wherein the first thickness is 6 mm to 10 mm and the second thickness is 2 mm to 4 mm.

20. The method of claim 15, further comprising one or more of the following:
- debriding at least a portion of debris on the nodules;
- removing debris from a surface of the tissue site;
- applying force to the tissue site through the perforations; and
- debriding the nodules.

21. The method of claim 15, further comprising channeling negative pressure through the plurality of perforations of the contact layer to generate concentrated stresses in tissue adjacent to the plurality of perforations.

22. The method of claim 15, further comprising distributing negative pressure to the tissue site through the contact layer.

23. The method of claim 15, further comprising venting the sealed environment, wherein venting the sealed environment comprises maintaining the sealed environment at ambient pressure for at least one minute.

24. The method of claim 15, further comprising fluidly coupling a solution source to the sealed environment and supplying fluid from the solution source to the sealed environment.

25. The method of claim 24, wherein supplying fluid to the sealed environment further comprises dwelling the fluid in the sealed environment for 5 minutes.

26. The method of claim 24, further comprising microfloating the contact layer within the sealed environment in response to supplying fluid to the sealed environment.

27. The method of claim 15, further comprising using a sharp debridement process to remove at least a portion of the debris.

28. A system for debriding a tissue site, comprising:
- a wound dressing of claim 1; and
- a cover adapted to form a sealed environment over the contact layer and the tissue site.

29. The system of claim 28 further comprising a fluid source adapted to be fluidly coupled to the wound dressing.

* * * * *

UNITED STATES PATENT AND TRADEMARK OFFICE
CERTIFICATE OF CORRECTION

PATENT NO. : 11,850,124 B2
APPLICATION NO. : 16/165457
DATED : December 26, 2023
INVENTOR(S) : Osborne et al.

It is certified that error appears in the above-identified patent and that said Letters Patent is hereby corrected as shown below:

In the Claims

<u>Column 28</u>
Line 31, In Claim 6, delete "Pharmacopeia 9"USP")" and insert -- Pharmacopeia ("USP") --, therefor.

Signed and Sealed this
Sixteenth Day of April, 2024

Katherine Kelly Vidal
*Director of the United States Patent and Trademark Office*